United States Patent [19]

Lehmer et al.

[11] Patent Number: 5,220,361

[45] Date of Patent: Jun. 15, 1993

[54] GAZE TRACKING FOR FIELD ANALYZER

[75] Inventors: Donald E. Lehmer, Berkeley; Alan R. Kirschbaum, Oakland, both of Calif.

[73] Assignee: Allergan Humphrey, San Leandro, Calif.

[21] Appl. No.: 710,722

[22] Filed: Jun. 5, 1991

[51] Int. Cl.$^5$ ............................................. A61B 3/02
[52] U.S. Cl. ................................ 351/226; 351/222; 351/224; 351/210
[58] Field of Search ............... 351/222, 223, 224, 226, 351/243, 210, 212

[56] References Cited

U.S. PATENT DOCUMENTS

| | | | |
|---|---|---|---|
| 1,960,111 | 5/1934 | Kirk | 351/224 |
| 4,145,123 | 3/1979 | Krahn et al. | 351/226 |
| 4,429,961 | 2/1984 | Sheingorn | 351/224 |
| 4,854,694 | 8/1989 | Hirano et al. | 351/224 |
| 4,950,069 | 8/1990 | Hutchinson | 351/210 |
| 4,973,149 | 11/1990 | Hutchinson | 351/210 |
| 5,066,117 | 11/1991 | Matsumura | 351/224 |

OTHER PUBLICATIONS

"Eye Monitor", Glenn A. Myers, Keith R. Sherman and Lawrence Stark, IEEE Journal, Mar. 1991.
ISCAN ® Eye Movement Monitoring Research Laboratory, brochure, 1989.

Primary Examiner—Rodney B. Bovernick
Assistant Examiner—Hung Xuan Dang
Attorney, Agent, or Firm—Townsend and Townsend

[57] ABSTRACT

A field test apparatus is disclosed which is interactive both in the automated positioning of trial lenses (used to correct the patient's focal distance to the tester hemispherical projection screen) as well as providing automatic gaze direction determination through automated video surveillance of the patient's eye. A moveable trial lens holder is provided. This trial lens holder is remotely moveable horizontally and vertically and carries light sources for illuminating the eye preferably in the infrared spectrum at oblique angles preferably towards the center of the eye from the periphery of the trial lens holder. In the gaze direction determination system, a gaze direction determination infrared source—preferably on the surface of the screen near the center of the screen—generates a gaze direction determination reflection on the cornea of the eye—this reflection being near the apex of a normal spherical cornea. At the same time, provision for the automated video measurement of the center of the eye pupil is provided—preferably including measuring a horizontal chord of the eye pupil, bisecting this horizontal chord, locating the bottom of the eye pupil along the bisected dimension, and thereafter finding the pupil center. The relative position of the gaze direction determination reflection from the cornea and the center of the pupil is necessarily related to the direction of gaze of the eye. This relative position is compared to the relative position that the patient initially had when properly fixated. Change in this comparison value is utilized to indicate a change in gaze direction.

33 Claims, 9 Drawing Sheets

FAR FROM LENS

NEAR TO LENS

GAZE TRACKING FOR FIELD ANALYZER

There is attached to this specification a microfiche appendix containing 1 page with 25 microfiche. This appendix is written in that computer language known as "C" on a compiler sold by SBE, Incorporated of Concord, California. When used to drive the position control computer 100, the overall function of the system herein describes results.

This invention relates to a field analyzer for testing the optical perception of the retina of the human eye. The disclosed apparatus for tracking gaze direction signals movement of the eye from the necessary straight ahead fixation required for accurate field test measurement.

SUMMARY OF THE FIELD TEST PROBLEM

A field analyzer is a device for surveying the sensitivity of a patient's retina. A spot of light, termed a point, is projected to a hemispherical projection screen for a short period of time. A patient viewing the hemispherical projection screen from the center of the sphere fixates along a line of sight to a fixation light source mounted on the surface of the bowl. The point of projection on the hemispherical projection screen controllably changes to positions spaced apart from the fixation light source. Preferably, the point is varied in intensity as the point moves from position to position on the hemispherical projection screen. A subjective determination is made by the patient in depressing a response button, if the point is seen. By positioning the point to known locations on the hemispherical projection screen and changing the brightness (in a total amount of about four decades), the sensitivity of the patient's retina is measured and mapped.

This simple concept has two basic optical problems interfacing to the patient. First, the patient must fixate on the center of the hemispheric projection screen. This fixation must be maintained when the point is presented usually to the side of the patient's fixated line of sight, if the point is to fall on a consistent part of the retina. Secondly, the patient's vision usually must be properly corrected to focus the surface of the hemispherical projection screen onto the retina.

It will be understood focus is particularly critical when the sensitivity of the retina is measured at the threshold of the patient's vision perception; where the patient's focus is not correct, targets that should be seen are not detected and give erroneous results. This is due to the fact that an unfocused spot of light appears dimmer than a focused one.

The patient's eyeglasses are almost always unsuitable for providing the focused view of the points on the hemispherical projection screen for at least three reasons. First, the frames of the patient's glasses will vary unpredictably in size and shape. They are an unknown in the areas of obscuration of vision and lens tilt angle. Moreover, it is vital that the conditions of testing be repeatable over a period of many years. This would be affected by changes in the patient's eye-ware.

Secondly, the optical prescription within the patient's glasses is almost always deficient for the particular focal distance (usually about 30 centimeters) required for the test. The glasses almost always do not correct the patients vision to the distance from the patient's eye to the surface of the screen.

Thirdly, the viewing angle of the patient's glasses is usually deficient. For example, the glasses of the patient may contain bifocal lenses or variable lenses which change the focal distance of the patient as a function of the point position on the screen. Where testing of the field of vision of a patient is being made, such glasses give erroneous results.

Because of these limitations, vision during a field test is typically corrected by so-called trial lenses which are selected to provide vision corrected to the 30 centimeter focal distance and placed near the eye in a trial lens holder. Moreover, two lenses are usually required, one to correct spherical power and one to correct cylinder (astigmatic) power.

The correction of the patient's eyesight is accomplished by adding one or two trial lenses to the optical path, directly in front of the patient's eye. These usually round lenses are made in a variety of sphere and cylinder powers and are selected by the operator based upon the patient's prescription, corrected to 30 centimeters, the radius of the hemispherical projection screen.

The standard trial lenses are relatively small in diameter (in the order of 2.5 cm). The center of the trial lenses should be placed in the approximate center of the eye to avoid prismatic effects associated With strong lenses. Additionally, the trial lenses should be close to the eye, to prevent the obscuring of the patient's vision by the trial lens holder or lens frame. Most field testing is done within a 30 degree angle from the fixation axis. Closeness is even more important when strong positive lenses are used as they make the viewing angle through the lenses smaller by magnifying the bowl.

In all known field test devices to date, the position of the lenses is fixed relative to the center of the screen, requiring the position of the patient's eye to also be fixed. This state is monitored by a video camera and presented to the operator as a surveillance tool. Movement of the patient's eye may require re-instruction of the patient by the operator.

Field analyzers typically use the ambient screen light for illumination of the video field. The ambient screen light of most field testers comes from the uniform illumination of the hemispherical projection screen surface, this illumination being provided to give uniform contrast to the projected points. It is also known to illuminate the eye from lights mounted on the trial lens holder using infra-red wavelengths to prevent the patient from detecting the lights.

In addition to the practical mechanical alignment problems attendant upon the use of trial lens, an additional problem exists regarding gaze direction in measuring the sensitivity of the patient's retina during the field test procedure.

Mapping the recognized variably positioned points on the spherical projection screen accurately onto corresponding positions on the retina requires that the eye does not change its angular relationship to the center of the hemispherical projection screen as the test progresses. The eye, however, is disposed in the head in such a way that changing gaze direction is easily accomplished, and in fact is the most natural thing to do when an object—such as a dim spot of light—comes into peripheral view. It therefore requires a great amount of concentration on the part of the patient to maintain a constant gaze direction. In short, the test procedure consuming normally up to 20 minutes for each eye can be very tiring on the patient.

In the normal field test the patient is asked to direct his vision straight ahead by "fixating" on an illuminated target. This positions the eye to image the target on the macula portion of the patient's retina, the area of the eye's highest resolution. Fixation on the center of the screen maintains a constant relationship between the points on the screen and specific locations on the retina, even with a change in the patient's head position from the central position.

It is known to check the patient's gaze direction by presenting points at the so-called optical cup or "the blind spot" of the patient's retina to be certain that such points are not seen. It is a well known natural phenomenon that overlying the optic cup on the retina of the normal eye there is an area where light is not seen. Near the beginning of a normal field test the position of the blind spot is determined by presenting many points near the expected position of said blind spot. It is assumed that the patient is properly fixated at this time. With the position of the blind spot of the patient determined, provision is made to present points periodically to this position in the hemispherical projection screen, which position will be "blind" to the patient's eye. Normally, and assuming the patient maintains correct gaze direction, this periodically presented point is not seen and a negative response is given by the patient to the presentation of the point. A positive response indicates that the patient is not maintaining correct gaze direction at the time of presentation to the "blind spot."

It is to be understood that the presentation of points of light to the blind spot adds time to the test. Additionally, such periodic presentations constitute only a spot check of gaze direction; the patient may have incorrect gaze direction for some interval in the temporal gap between successive spot checks. At present, measuring actual gaze direction is not in common use in commercial field testers.

There are some field test instruments which measure loss of a central pupil position and claim they are measuring gaze direction. This measurement does relate to the trial lens centering issue, reporting the patient is, or is not, centered on the trial lens, but has no bearing on the actual gaze direction. It is to be understood that the eye can be gazing in virtually any angular direction with the pupil perfectly centered in the trial lens.

During field testing, it is known to observe the eye under test in a video presentation. This enables the operator to have a continuous view of the patient's eye position with respect to the trial lens holder to detect obvious deficiencies in the field test. Unfortunately, the operator may be either periodically absent or attending other tasks which divert his attention from the video presentation. Further, the operator cannot determine gaze direction from the video display and typically is unaware of when the actual point is presented, the only time when gaze direction is important. Only pupil position can be reliably measured. There is, however, a natural relationship between eye movement activity and the likelihood of satisfactory gaze direction performance. Such video presentations require a video camera and sufficient light for the video presentation to be accurately recorded.

Field analyzers are known that illuminate the hemispherical projection screen with an even field of light generated by incandescent lamps which contain some infra-red energy. Typically, the video camera used is sensitive in the infrared spectrum. This increases the contrast for patients with a dark colored iris between light reflected from the iris and the dark pupil, as all iris colors reflect about the same amount of light with infrared illumination.

However, this illumination system also reflects light from the trial lens surface. The hemispherical projection screen partly surrounds the lens. The lens is typically not anti-reflection coated. Therefore the lens glows with infrared light captured from the hemispherical projection screen. This glow from the lens reduces the pupil to iris contrast in the video image.

SUMMARY OF THE INVENTION

A field test apparatus is disclosed which is interactive both in the automated positioning of trial lenses for providing the correct focal distance to the hemispherical projection screen as well as providing automatic gaze direction determination through automated video surveillance of the patient. A patient chin rest is provided, with two chin rests or chin indentations, one chin indentation for testing of each eye of the patient. The patient typically has his chin placed in the chin indentation required for testing of the left eye or the chin indentation for testing the right eye. The chin indentation or rest is typically initially adjusted in elevation to proximately center the patient's eye with respect to the center of the spherical projection screen. This adjustment is made by the operator by either viewing the patient and the trial lens holder from the side, or by using the video display monitor image. This adjustment is required due to the wide range in vertical spacing from the patient's chin to the patient's eye. The variation in horizontal spacing between the left and right eye being tested is more uniform, and does not require operator adjustment over the population tested by the field test apparatus.

A moveable trial lens holder is provided. Testing occurs, one eye at a time. This trial lens holder is remotely moveable in the horizontal and vertical direction and carries small light sources, preferably within the infrared spectrum, for illuminating the eye being tested.

The sources are preferably located at the 2, 4, 8, and 10 o'clock positions with respect to the trial lens center. The reflections formed by these sources in the cornea may be used as an indicator of eye position, but the eye position is preferably determined by locating the pupil itself in the video image. The trial lens holder is provided with an indication of location with respect to the video image. This indication of location data can be used by the positioning computer to locate the trial lens holder and to restrict the area of interest of the video data to the area inside the trial lens. Preferably, the trial lens holder is provided with a source of illumination—again in the infrared spectrum—directed into the video camera to determine trial lens location. This illumination source produces a bright spot of light in the video image which moves with the trial lens holder, and is termed the "marker." The patient's head is initially aligned vertically by the operator vertically positioning the chin rest prior to the start of the field test. The patient is then requested to look through the trial lens by moving his head, if necessary. The positioning computer determines the presence of an eye in a video window equal to the size of the trial lens and positioned inside the trial lens by the data obtained from the trial lens marker. The positioning computer then moves the trial lens holder horizontally to center the pupil of the eye in the lens. During the test the system follows (tracks) the pupil.

As a result the trial lens follows inadvertent patient head movement without otherwise interrupting the field test. The moveable trial lens holder is advantageous to the disclosed gaze direction detection system. It adds the assurance that the pupil is central to the lens, and that an additional video window can be generated which is reduced in size to encompass only the center of the lens, preventing possible reflections from the trial lens surface from confusing the gaze direction measurement.

In the gaze direction detection system, a gaze tracking infrared spectrum source, such as a light-emitting diode (hereafter, LED)—preferably on the surface of the screen near the center of the screen—causes a gaze tracking reflection on the cornea of the eye—this gaze tracking reflection being near the center of a normal spherical cornea. This reflection is small in diameter and its position is independent of closeness of the eye to the trial lens holder and position of the eye with respect to the center of the projection screen.

This source is provided with a means of turning the source on and off, such that the reflection from the cornea is generated only when needed for gaze direction determination. This can occur in a single video frame and separation can be accomplished by subtracting one video frame from a previous video frame. The only change in the small central window should be the addition of the corneal reflection from the gaze tracking source.

The gaze tracking source should not be on during lens tracking since it generates reflections in the trial lens which may confuse the determination of the pupil center. These reflections are prevented from being in the small central video window by tipping the trial lens in the trial lens holder at an angle with respect to the video camera and light sources.

To measure the gaze direction, the center of the pupil must also be determined with precision greater than that needed for lens centering. Provision for the automated video measurement of the center of the eye pupil is provided—preferably including measuring a horizontal chord of the eye pupil, bisecting this horizontal chord, locating the bottom of the eye pupil along the bisected dimension, and thereafter finding the pupil center.

The gaze direction is determined by the vector displacement between the pupil center and the gaze tracking corneal reflection. An initial value for this vector is determined at the start of the field test when it is assumed that the patient has a proper gaze direction. Change in this displacement vector is utilized to indicate a change in gaze direction. The disclosed gaze direction determination presupposes correct trial lens centering in a protocol that ignores reflections that can possibly be present in the trial lenses required. Provision is made to make a record of trial lens movement and gaze direction change to determine quality of the data obtained during the field test.

Other objects, features and advantages will be more apparent after referring to the following specification and drawings in which.

DESCRIPTION OF THE PREFERRED EMBODIMENT

Figure 1A:
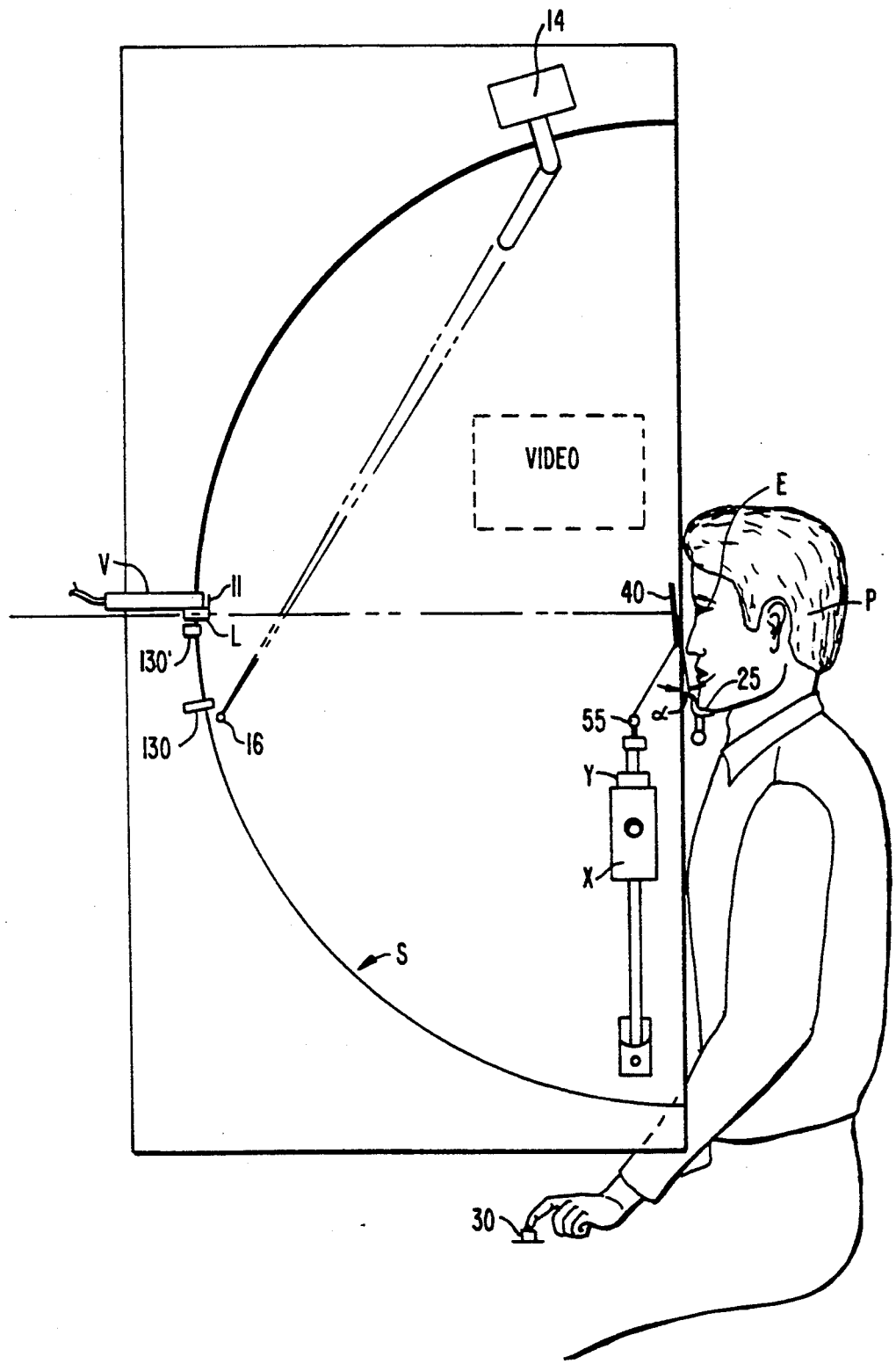
FIG. 1A and 1B are respective side elevation and elevation views of a patient looking into a field tester having a hemispherical projection screen, the patient in FIG. 1B being positioned for the conduct of the field test of the retina of his left eye utilizing the monitoring video equipment and moveable trial lens holder disclosed in this invention.
Figure 1B:
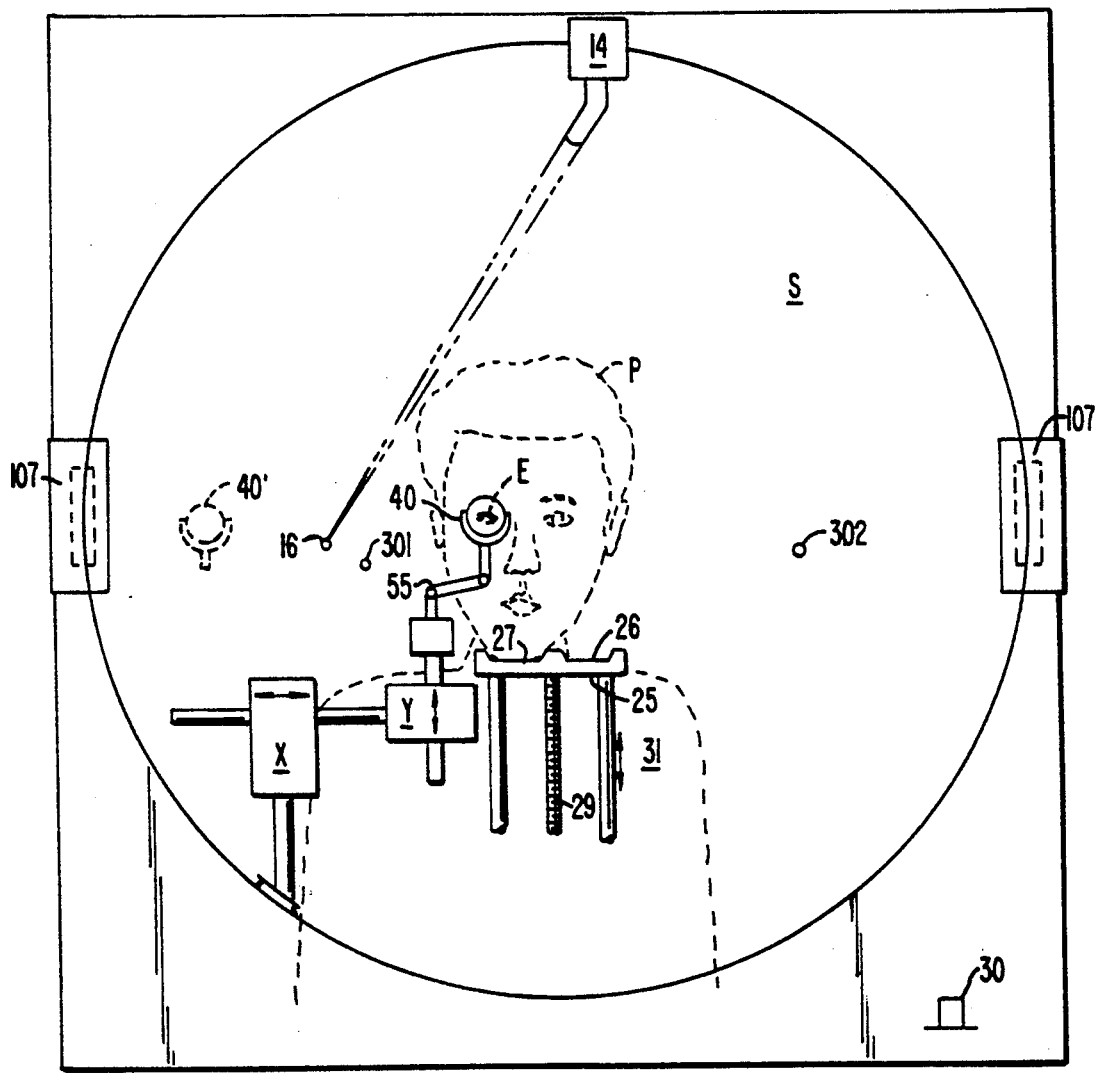

Referring to FIGS. 1A and 1B, a schematic of movable trial lens holder 40 of this invention is illustrated. A patient P is illustrated observing a hemispherical projection screen S. Patient P is here illustrated having left eye E being tested. In this test the patient P has been directed to fixate on the fixation light L at the center of the hemispheric projection screen.

Referring to FIG. 1B, the chin rest 25 illustrated has two indentations, these indentations including indentation 26 for testing the patient's right eye and indentation 27 for testing the patient's left eye. The chin rest is adjustable vertically in the direction of arrow 31 on threaded rack mechanism 29. Other than the two chin rest indentations, no horizontal correction of the position of the chin is provided.

Projector 14 under the control of a computer (not shown) well known and understood in the prior art projects spot 16 of the light on the surface of the hemispherical projection screen. The patient indicates that the spot 16 of light was seen by depressing response button 30. The response of the patient in pressing the button is recorded by apparatus well known and understood in the prior art.

The field test apparatus illustrated is old. It may be purchased from Allergan Humphrey of San Leandro, California, USA under the designation Field Analyzer Series 600. In what follows, the reader will understand that the mechanism for moving the trial lens holder and the tracking of the gaze direction utilizing video camera V, FIG. 1A, constitutes the primary novel portions of the disclosure herein.

Figures 2, 3A:
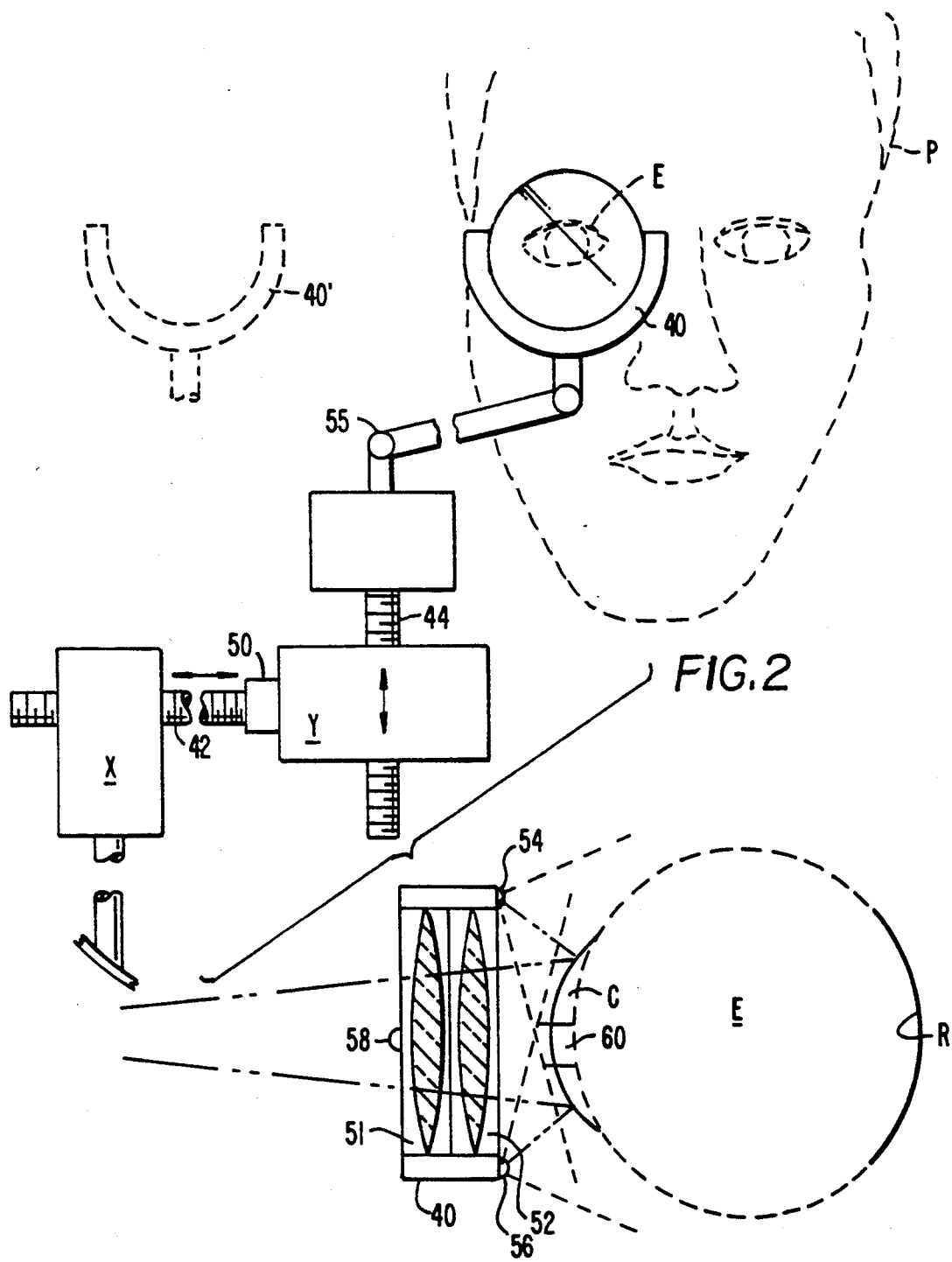
FIG. 2 is a schematic illustrating the apparatus for effecting trial lens movement to follow the eye of the patient during inadvertent motion of the head and eye occurring during the duration of the, field test of the eye.
FIG. 3A and 3B are schematic representations of the trial lens illumination sources shown as four LEDs pointing toward the eye for the illumination of the eye with FIG. 3A being a representation of the trial lens holder and eye viewed from the top and FIG. 3B illustrating just the trial lens holder from the side facing the patient.

Trial lens holder 40 is shown in FIG. 2 as a semicircular frame. Holder 40 has an active and inactive position. In the active position, trial lens holder 40 has the possibility of moving both horizontally and vertically under the control of two motors, X and Y. When the trial lens holder 40 is in the inactive position, the holder is moved out of the central position to an extreme position shown in broken lines at 40' where the trial lens holder is not in the field of view of the patient P during testing.

The reader will understand that field testers are used for two types of field test. The most frequently done field test tests the central 30 degrees from the fixation axis The less frequent test makes measurements of visual sensitivity at viewing angles between 30 and 90 degrees from the fixation axis, to test the sensitivity of the peripheral vision. For this kind of testing, lens holder 40 is moved to the position of lens holder 40' shown in broken lines. Typically in this extended field of vision testing no trial lenses are utilized. Otherwise the points presented to extreme angles on the screen would not pass through the viewing angle of the lens. Some of the points would not be corrected by the lens and some would be obscured by the trial lens frame.

More normal field testing consists of measuring the central vision sensitivity within a 30 degree angle from the fixation axis. It will hereafter be assumed that this measurement is the measurement of interest unless specifically otherwise stated.

Referring to FIG. 2, a mechanical schematic is illustrated setting forth the mechanism for the required movement of trial lens holder 40. The mechanical schematic shows the X motor with the body of said motor connected to the chassis of the field tester. The shaft 42 extending from the X motor contains a fine external thread. The shaft passes through the X motor which contains a nut which is rotated by the rotor of the X motor. Since the shaft is prevented from the rotating by the mechanism, the rotation of the nut causes translation of the Y motor responsive to rotation of the X motor rotor. As the X motor rotor rotates, the shaft 42 moves the Y motor horizontally.

The Y motor is of similar design and is mounted on a horizontally sliding carriage 50 driven by the X motor. The Y motor is capable of moving the trial lens holder vertically via vertical shaft 44. The illustrated method of vertical movement is precisely analogous to the similar horizontal movement of the X motor.

The illustrated mechanism typically uses conventional linear stepper motors. These stepper motors allow the controlling computer system described below, to move the lens to any position necessary in a vertical plane in front of the eye for all normal excursions of movement of the patient's eye E.

Figure 3B:
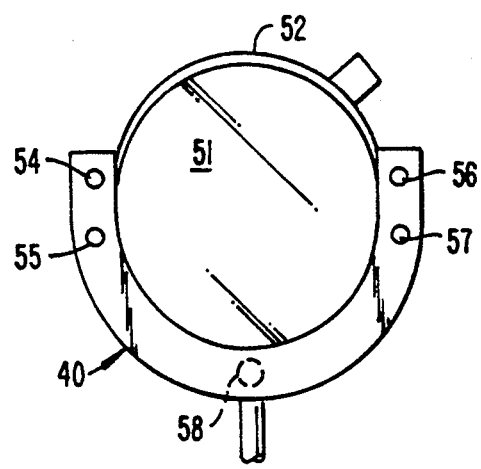

Referring to FIGS. 3A and 3B moveable trial lens holder 40 can be more completely understood. Trial lens holder 0 is here provided with an infrared light source 58 pointing directly at the video camera V. This source 58 is termed a "marker."

We prefer the use of the marker 58 for tracking of the position of the trial lens holder 40. The reader will understand that other expedients will work as well. For example, the mechanical position of the lens holder 40 could be input by other means—for example counts of stepper motor rotation. For the purposes of the understanding of the invention here disclosed, all that is required is that the position of the lens holder 40 with respect to the video image of the eye E be ascertainable.

At least one and preferably four infrared light sources 54-57 are placed in the trial lens holder at the respective 2, 4, 8, and 10 o'clock positions. These sources are aimed obliquely towards the pupil center to illuminate the iris evenly. Although the reflections created in the cornea by these sources can be used to define the eye position, extraneous corneal reflections are sometimes present which can be confused with these primary ones. It is therefore preferable to locate the eye using the pupil itself, which appears as a large dark area in a generally light field of the iris, and is therefore easily distinguishable.

The positioning of the light sources at the 2, 4, 8 and 10 o'clock positions is preferred. It has been found that light sources above the eye cause shadows cast by the upper eye lid and eye lashes. Similarly, lights below the eye have similar shadows cast by either the lower eye lashes or the flesh of the eye. Further, many eyes are partially closed—especially at the upper lid in the observing state. This being the case, it has been found that light incident on the eye E from the side has the least chance of interference by the surrounding body parts. When the marker 58 is used, a video processor determines the relative location of the marker and the eye pupil 60. The processor maintains an initially determined spatial relation between the eye pupil 60 and marker 58 by automated following movement of the trial lens. As a result, the trial lens is automatically centered to the eye pupil during the field test procedure.

It will be understood that an advantage of the disclosed trial lens centering is that it prevents obscuration of portions of the patient's field of view by the trial lens holder 40 which might otherwise occur if the lens became off center relative to the patient's eye E. At the same time, the automated movement of the trial lens increases patient comfort and reduces the patient's stress by not requiring an absolute and frozen head position for the test duration of up to twenty minutes. As a result, both patient comfort and test accuracy are improved.

An additional advantage is that minor movements of the eye relative to the field tester hemispherical projection screen do not appreciably alter the accuracy of the test, if proper gaze direction is maintained.

An additional advantage of the disclosed automated trial lens centering protocol is that the patient's head need only be adjusted in elevation with respect to the center of the field test screen. Further, the requirement for the operator to adjust the horizontal position of the patient's head at the beginning of the test is eliminated by the chin rest 25 having the dual chin rest indentations 26, 27. As a consequence, the prior art mechanism to adjust the head position horizontally is no longer required. As this horizontal head adjustment mechanism is required to be both sturdy and adjustable, the not inconsiderable cost of the mechanism can be saved by its omission.

For the normal testing protocol, vision is tested only within a 30 degree angle from the fixation axis. There are however, some testing protocols that extend the testing angle outside of this angular range, approaching 90 degrees from the fixation axis. For these peripheral testing protocols, the trial lens holder 40 cannot be entirely out of the field of view. For this reason the trial lenses 51, 52 and trial lens holder 40 are typically not used and are moved entirely out of the patient's field of view. This removes the illumination source for the eye, since the source is mounted on the trial lens holder. These illumination sources are instrumental in illuminating the iris-pupil boundary for the determination of the pupil center used as part of the data in gaze direction determination.

Two alternatives for maintaining the determination of pupil center without the trial lens holder present around the eye are disclosed. One alternative is to modify the lens holder 40 such that the illumination source LEDs are mounted separately from the lens holding portion and below the field of view, thus allowing the lens holding portion of the lens holder 40 to be removed for peripheral testing. This requires the LEDs to direct light upwardly onto the eye from a position underneath the eye. This alternative has the disadvantage of causing a shadow to be created by the flesh below the eye, making the definition of the iris/pupil boundary difficult at the bottom edge.

A more advantageous alternative is to place two additional LED sources 301, 302 (See FIG. 1B) on the screen S. These sources are sufficiently off center in the bowl to illuminate the eye from the bowl surface and not cause reflections from the cornea in the central area which would conflict with the gaze tracking source. Placement of these sources on the bowl surface is possible in the peripheral testing case since there are no trial lenses to cause unwanted reflections. The central corneal reflection for the determination of gaze direction is still generated in the same manner.

As shown in FIG. 1A, 1B and 2, the Z adjustment, the closeness of the lens to the eye, is adjusted manually. This is in the form of a high friction connection 55 near the base of the connecting arm, allowing the holder to be moved closer to the eye by changing the angle of the connecting arm.

Referring to FIG. 3A and 3B, a schematic of the eye E illumination sources in the lens holder is illustrated. This schematic drawing shows both a top view of the patient's eye E and a view of the lens holder 40 from the patient's point of view. FIG. 3A is a top view showing two trial lenses 51,52 mounted in the trial lens holder 40.

Typically, the first trial lens 52 provides the sphere correction required by the patient. The second trial lens 51 has the requisite cylinder component of the patient's correction and is aligned at an appropriate angle for said patient's correction. The lenses 51, 52 are shown disposed in front of the cornea C and retina R of eye E.

Referring to FIG. 3B a patient's view of tne lens holder 40 is illustrated. This lens holder shows the position of the four infrared light emitting diodes (LEDs) 54–57. These LEDs are integral to the lens holder 40.

For the purpose of eliminating reflections from the trial lenses, the eye is illuminated from the trial lens holder using the preferably four infrared light emitting diodes (LED's) located on the side of the trial lens holder facing the patient. The preferred positions of these LED's are at the 2, 4, 8, and 10 o'clock positions about the center of the trial lens holder.

The infrared LEDs are encapsulated in one of many standard packages and inserted into the lens holder frame. The LED selected is not equipped with a lens, or a very low power lens, such that the light spreads out in a wide angle pattern. The four patterns overlap to illuminate the eye with an even illumination producing a high contrast video image in the infrared spectrum.

Referring to FIG. 3A, it will be understood that cornea C of eye E is a highly reflective spherical surface which reflects certain of the rays from the infrared illumination sources to the video camera V. These rays follow the equal angle rule, reflecting from the surface of the cornea C at an angle equal to and opposite from the incident angle. Four bright dots of light 64–67 are formed in the video image of video camera V in addition to the normal view of eye E and surrounding areas. This can be seen in FIG. 4.

Note that there are no reflection rays generated near the center of the cornea. Further, there are no reflection rays generated by the surfaces of the trial lens. The lack of reflection of the illumination LEDs near the center of the cornea is due to the illumination source's angle to the cornea. The lack of reflection from the lenses is due to the fact that the illumination sources on trial lens holder 40 are on the patient's side of the lenses.

It can further be observed with respect to FIG. 3A, the angle of the illumination sources also precludes the light reflected from the retina R of the eye E from reaching video camera V. This allows the video image to contain a dark pupil area free of reflections, a desirable image for the pattern recognition activity of the position control computer system designed to center said trial lens on the pupil.

Figure 4:
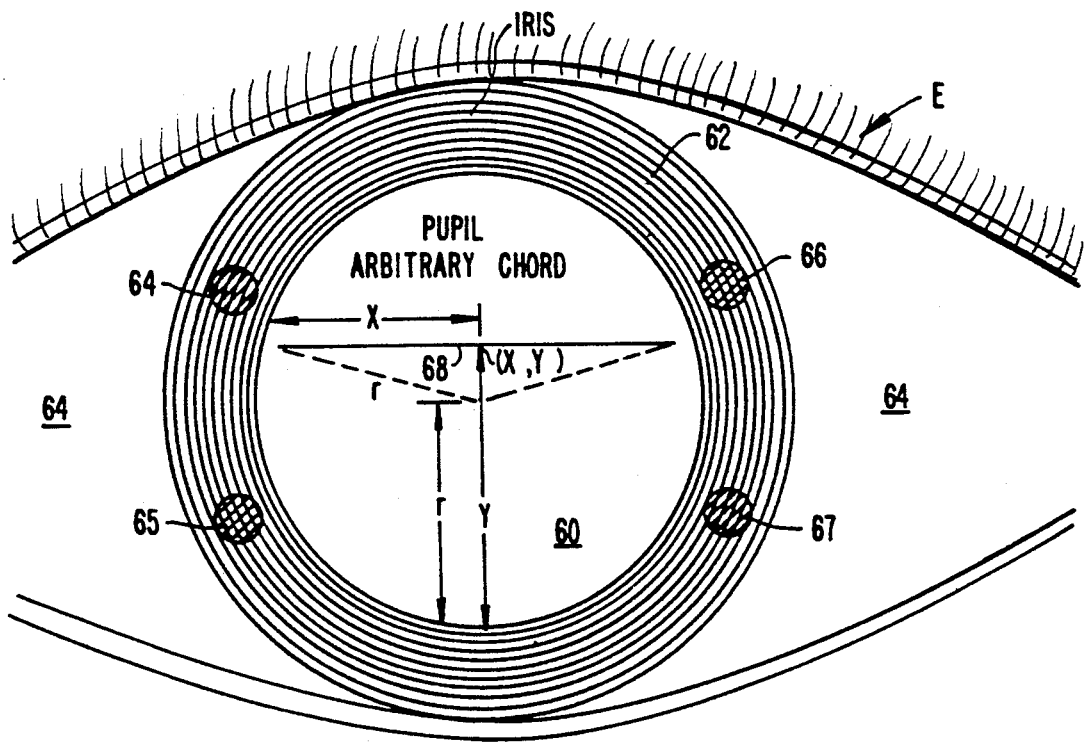
FIG. 4 is a schematic diagram of the iris and pupil of an eye being tested, the schematic there illustrating the dimensional analysis for determining the radius and the center of the pupil of the eye.

Referring to FIG. 4, a schematic of iris and pupil with center finding chord utilized in the computation of the center of the pupil 60 is illustrated. This schematic shows an idealized video image of the dark pupil 60 surrounded by an illuminated iris 62. The four black dots 64–67 appearing in the iris 62 area are the reflections from the spherical surface of the cornea C of the respective illumination sources 54–57 from the lens holder 40.

It will be understood that the presentation of the eye E on paper differs from reality in that the pupil 60 is dark, the iris 62 is about one-fourth brightness, the sclera 64 and surrounding skin are about one-half brightness, and the four corneal reflections 64–67 are full brightness.

It is a purpose of this invention to use wavelength and video windows to segregate light from the various sources to reduce interference in the video data. To reduce the trial lens reflections and to further increase the contrast of the iris and the pupil, the video camera responds only to infrared light. Preferably, the video camera includes an infrared band pass filter 11 to achieve this result. See FIG. 1A.

Referring to FIG. 1B, it is preferred to illuminate the hemispherical projection screen S with an illuminated background of relatively constant luminance in the visible spectrum. The screen lights 107 illuminating the screen area are fluorescent, to reduce the infra-red content in the hemispherical projection screen S. It will therefore be understood that light reflecting from objects illuminated by the screen lights will not appear in the video data. As a result, an unobscured view of the eye E and the iris 62/pupil 60 boundary are provided behind the trial lenses, which lenses are for practical purposes transparent in the video display.

An advantage of the placement of the illumination sources within the trial lens holder is that the camera views the eye being tested (through the trial lenses) using illumination which remains constant, independent of trial lens holder position with respect to the center of the bowl. Consequently, variation of eye illumination does not occur with variation of eye position.

Utilizing the disclosed illumination scheme it will be understood that the video camera V generates data when viewing the area of eye E being tested through the trial lens holder 40. When the video data is restricted to the area overlapping the trial lens (see FIG. 5A and 5B), the data contains at least the following:

1. A dark area in the position of the pupil 60 caused by fact that the illumination sources are pointed at a oblique angle, resulting in little or no light reaching the part of the retina viewed by the camera. The resulting dark pupil 60 and bright iris 62 contrast is most beneficial for determining the pupil location and, as will hereafter be realized, the gaze direction of the eye being tested.

2. A brightly illuminated iris area 62, this iris area having the property of forming a sharp delineation from the dark pupil.

3. Reflections of the LED's 54-57 at points 64-67 created by the spherical cornea acting as a mirror reflecting the image of the small LED sources 54-57.

If the video area is not restricted to the area overlapping the trial lens, the following additional data is available:

4. A small bright area preferably below the trial lens created by the lens holder marker LED 58.

5. A composite high contrast image of the eye E and surrounding trial lens holder 40 to enable convenient operator monitoring of the patient on the operator CRT display during the field test.

An additional advantage of the disclosed video protocol is that data in the camera field can be easily computer analyzed to find the brightest and darkest areas. The last bright video area, scanning from top to bottom, is the marker LED 58. This location is used, in conjunction with a constant offset, to define a video window 115 which restricts the video data to that falling inside the trial lens opening. This prevents the dark area created by the trial lens holder and reflections from the trial lens frame from being considered in the computer analysis. The pupil is the only major dark area in the window and the marker is the last major bright area in the video field. This bright area, which is the image of the "marker" LED 58, moves if the trial lens holder is moved. The position control computer automatically moves video window 115 to have a constant offset from said marker position.

An advantage of the trial lens centering protocol, is that the reflections from the illumination sources need not, and preferably do not, fall inside the pupil area. Consequently, and referring again to FIG. 1A, another infrared light source 130 can be placed on the surface of the screen, near the center, to form an additional reflection from the cornea in the dark pupil area. This light source 130 can create a reflection central to the cornea as at reflection 140 (see FIG. 7A) for gaze direction determination. It will be shown that this reflection is separate from and in non-interference with the reflections created by the four illumination LEDs 54-57.

This light source 130 creates reflections from the surface of the trial lens and from the trial lens frame. The former is deflected from the central area by tilting the lens at an angle, preferably down, and the latter is excluded by the large video window 115 being centered within the trial lens frame (see FIG. 5B).

Figure 7C:
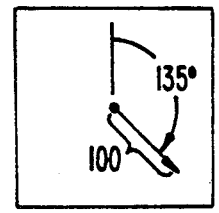
FIG. 7C is an enlarged view of the vector of FIG. 7B illustrating the determination of the change in gaze direction.
Figure 7A:
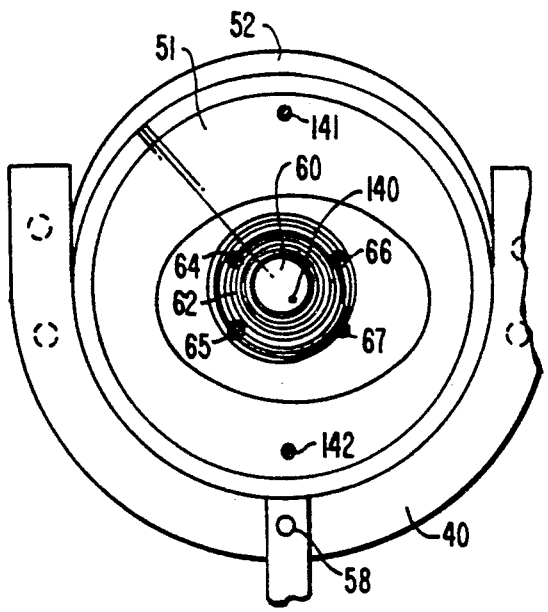
FIG. 7A is an illustration of the trial lens holder illustrating corneal reflection from the four illumination LEDs and from the gaze tracking light source during gaze direction determination.
Figure 7B:
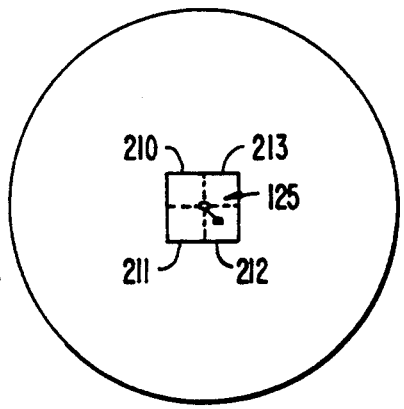
FIG. 7B is a representation of the video window relative to the trial lens holder illustrating by way of a vector the change in the direction of gaze of the patient.

An advantage of the lens centering protocol is that the pupil is always in the center of the lens, allowing any additional reflections created by light source 130 to be rejected by a small video window 125 in FIG. 7B, placed in the center of the trial lens for gaze determination. Furthermore, if the eye is not in the center of the lens, corrections to the position of the reflection 140 due to the refractive effects of the lens must be made. Therefore, an additional advantage of the lens centering protocol is to minimize these corrections.

An additional object of this invention is to disclose broad protocols for the centering of the moveable trial lens with respect to the eye. In this simplest protocol, the hardware/software system must be aware of the absolute relationship between the position of the lens holder in the video data and the position of the trial lens holder 40 with respect to the field tester frame. In the use of such a system, initialization occurs moving the trial lens holder 40 to a known position with respect to the field tester frame, and a pre-determined offset is used to position the video window to be central to the trial lens. Thereafter, discrete movement of the trial lens holder is made to keep the trial lens centered on the pupil.

It will be understood that such a system could easily get out of position by mechanical interaction with the patient. A second protocol would be to measure in real time the absolute position of the lens holder with respect to the field tester frame, using position encoders of some form. A third, and preferred, protocol for measuring the relative position of both the trial lens holder 40 and the eye E can occur utilizing marker 58 on the trial lens holder 40. With any of the protocols, centering of the trial lens to the pupil of the eye occurs.

The video image is formed by scanning the brightness of the scene horizontally into discrete areas, termed lines. A combination of many of these lines, one below another, forms a complete scan of the image. This data is serial in nature, that is, one line after another, and is converted to a digital form and stored in a block of electronic memory. This forms a parallel form of the image for the analysis by the computer.

For the analysis of the video image used herewith, a video RAM was utilized that is a commercial item of manufacture. Specifically, a video RAM model MIP-512 sold under the mark Matrox, and manufactured by the Matrox Company of Dorval, Quebec, Canada.

The process of finding the pupil center begins by selecting the data on a video line which by the nature of the scanning process forms a horizontal chord located arbitrarily within the pupil. To obtain the best accuracy the position control computer selects this line as being the longest dark area in the video data, normally the major diameter of the pupil.

Referring to FIG. 4, the computer proceeds to find the ends of said chord 68 by finding the transition from the dark pupil area 60 to the lighted iris area 62. It is preferred to use the second derivative function of the light values to find the point of transition independent of brightness and to a resolution beyond the individual pixel resolution.

Figure 11A:
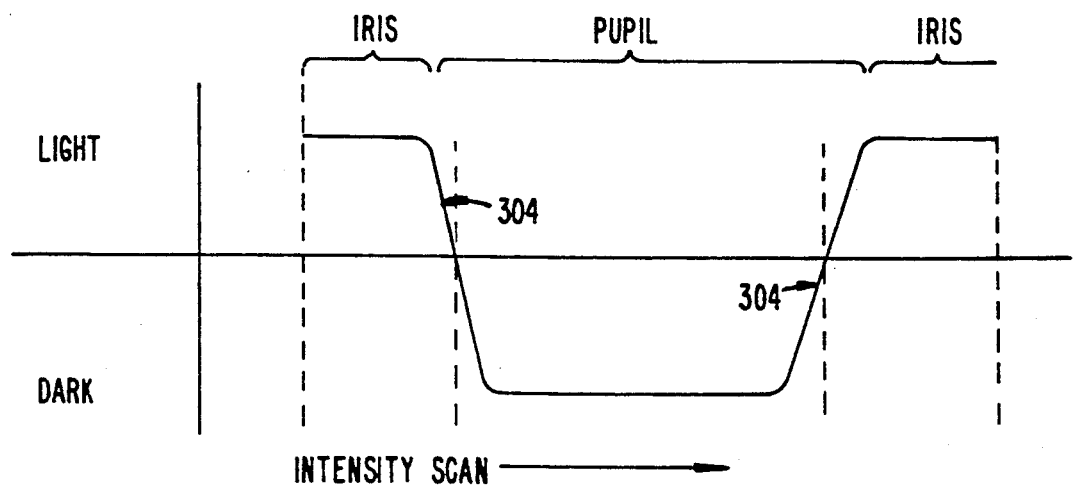
FIGS. 11A–11C represent the video data on one video line passing across a diameter of the eye illustrated in FIG. 4 taken through the iris and pupil, the figures setting forth light intensity in FIG. 11A, the first derivative of light intensity in FIG. 11B, and the second derivative of light intensity in FIG. 11C.

Referring to FIG. 11A, we illustrate the light intensity on a specific video line from the camera as a function of time. The line selected is near the arbitrary chord of the pupil illustrated in FIG. 4. As can be been, the intensity of the data corresponds directly to the brightness of the image. If this signal were to be used for the location of the pupil, a specific intensity 304 could be selected. However, in practice the data is not as ideal as shown in FIG. 11A, typically exhibiting a variation in the brightness of the iris from the left side to the right, and a variation in the rate of change in brightness in the pupil/iris boundary on left and right sides. This would not be uniform for all eyes and all illumination conditions. Therefore, this format is not preferred.

Figure 11B:
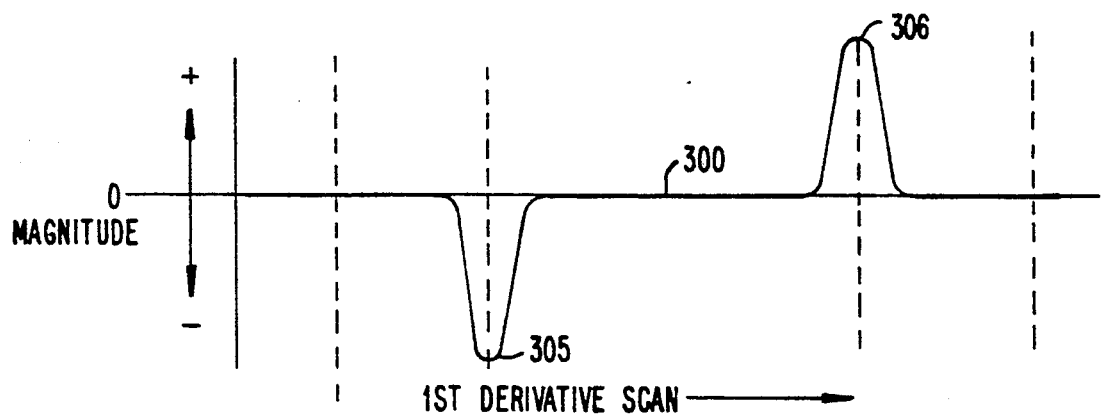

Referring to FIG. 11B, the first derivative of the signal presented in FIG. 11A is illustrated. This produces peaks 305, 306 extending in opposite directions with respect to the horizontal baseline 300.

Figure 11C:
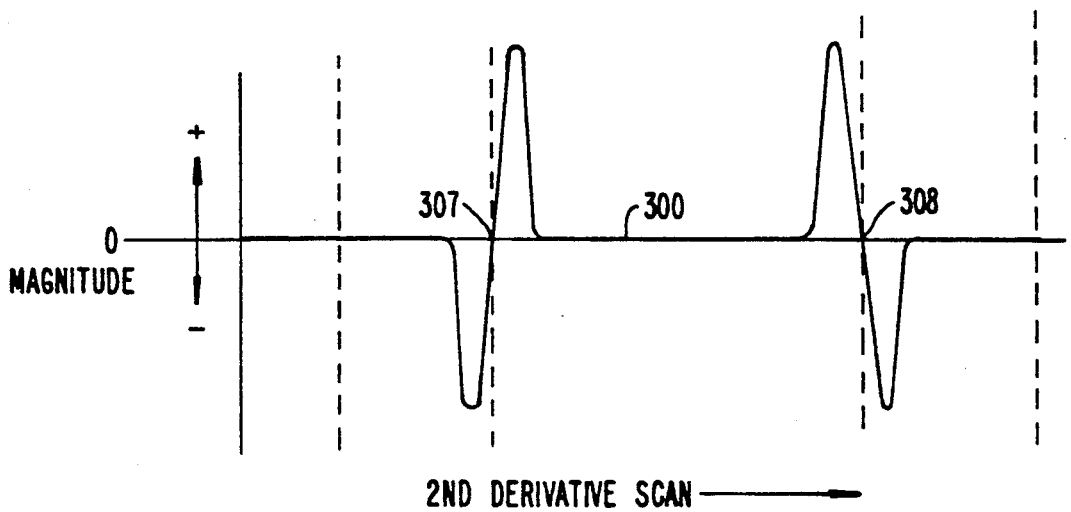

Referring to FIG. 11C, the second derivative is illustrated. This signal is preferred as the border crossing detection method from the iris to the pupil (on one hand) and from the pupil to the iris (on the other hand) because the points 307 and 308 at which the signal crosses the baseline 300 are independent of signal strength and iris brightness since these points are based on rate of change of brightness rather than absolute brightness. Further, the signal from eyes of varying colorations will be uniform in the crossing of the horizontal axis at 307 and 308. The length and position of the ends of chord 68 is determined by points 307 and 308 on the specific horizontal video line selected.

Referring to FIG. 4, the next step in the process is to bisect chord 68 and starting at said bisect scan down a vertical line to find the transition from the dark pupil to the lighted iris area at the bottom of the pupil 60. This generates the vertical distance (y). The horizontal distance (x) is the length of the chord from the bisect to one end of the chord 68.

The calculation is based on the Pythagorean theorem. As is well known, the sum of the squares of the two sides of a right triangle equals the square of the hypotenuse. The triangle is shown in FIG. 4 formed by half of the chord 68, the difference between the vertical component and the unknown radius (y−r), and the unknown radius (r) as the hypotenuse. This is only true if the pupil is a true circle, an assumption for this measurement. The mathematical method applies equally well to an arbitrary chord 68 placed below the pupil 60 center.

The formulation for this is as follows:
By the Pythagorean Theorem:

$$a^2+b^2=c^2$$

$$(y-r)^2+x^2=r^2$$

$$y^2+r^2-2yr+x^2=r^2$$

$$2yr=x^2+y^2$$

$$r=(x^2+y^2)\div(2y)$$

$$Center = Xo, Yo-(y-r)$$

Where
r = unknown radius
x = half of the chord length
y = distance from chord to bottom of pupil and
Xo,Yo = location of arbitrary chord bisect A further object of this invention is to disclose the determination of gaze direction independent of pupil diameter. Since the pupil diameter changes during the test, any method for finding the gaze direction must be independent of pupil diameter. It is also incidentally desired that at the pupil diameter be determined by the system and reported to the main computer for recording the physiological function of the light response of the pupil. Determination of the pupil center can be done by many methods, in addition to said method, such as, bisecting the X and Y major diameters, locating many points on the pupil boundary and calculating the center, or positioning a circular video mask to obscure the pupil.

An additional object of this invention is to disclose a preferred method for the location of the center of the pupil which is implemented in the disclosed software with this invention. It will be understood that the upper eyelid of the patient may come down during the test to partially obscure the pupil. This condition may constitute a temporary impediment to the test or alternatively may constitute a permanent condition of the patient under test. This is allowable for pupil diameter determination so long as the central reflection is not obscured. When obscuration of the central reflection occurs, the system must cause an error, indicating that gaze direction cannot be determined, until a central reflection is found again. This obscuration of the central reflection most commonly occurs when the patient closes an eyelid.

The preferred process for determination of pupil center is as follows:

1. Illuminate the eye with preferably four LED's 54-57 to produce uniform iris illumination.

2. Analyze the video data from the bottom up, finding the line(s) and horizontal cells (pixels) containing lens holder marker 58, based upon brightness. The first bright area is the marker, since it is below the trial lens and therefore below the reflections of the illumination sources 54-57.

3. Position the lens window 115 to exclude the video data outside of the trial lens circle using the position of the marker found in step 2.

4. Find the specific video line containing the longest dark area within the window and determine the position of the bisect of said line.

5. If gaze direction determination is not scheduled, said bisect is used to reposition the lens if necessary. This is determined by comparing the location of said bisect and the location of the trial lens marker. If the offset exceeds a maximum allowable limit, the lens is moved to center on said bisect to correct the error.

6. If gaze direction determination is scheduled, a more accurate pupil center must be found. The method starts with the longest video line which was selected in step 3.

7. Determine the number of pixels on this chord to the pupil to iris transition in both horizontal directions. It will be remembered that in the preferred embodiment, the transition between the preferably dark pupil and the relatively bright iris will be easily detectable.

8. Bisect the number of horizontal pixels to find the horizontal position of the center of the chord. This is assumed to be the horizontal center of the pupil.

9. Analyze the data on a vertical line through the bisect in a downward direction to find lower edge of the pupil.

10. Calculate the center of the pupil and the diameter.

11. Turn on gaze direction determination LED at the end of the video frame A and maintain the illumination during video frame B, the next frame. Subtract frame A data from the frame B data to find the only new event in the small central window 125 in FIG. 7b, the central gaze direction determination reflection.

12 Compare the displacement vector from the pupil center and gaze direction determination reflection position to that stored from the initial determination. Create error if gaze direction is outside of a pre-determined limit.

As noted above, the determination of pupil diameter may be done in the lens centering portion of the system schedule and the gaze direction determination reflection position may be determined during the gaze direction determination portion. This allows the gaze direction determination reflection to fall on, or outside, the pupil without disruption of the pupil center determination. The gaze determination must be made rapidly, preferably during two camera frames (0.067 seconds), such that the data is valid directly before and during the 0.2 second point presentation. If gaze direction determination is scheduled the system will alternate between measuring the pupil diameter and center and measuring the gaze direction determination reflection position. The lens centering portion of the system schedule may be terminated to prevent distraction of the patient whenever a point is presented on the screen.

Figure 5A:
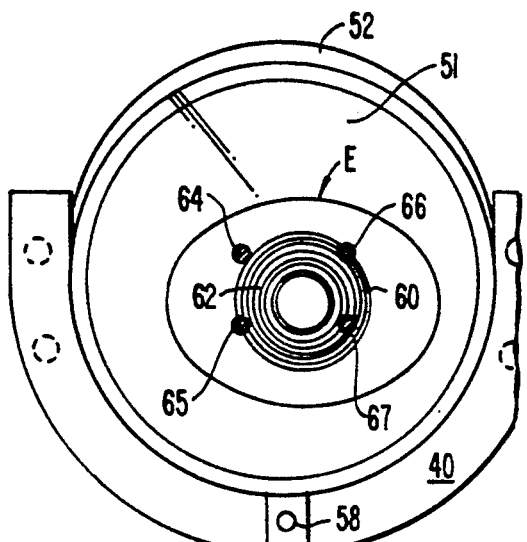
FIG. 5A is an illustration of the trial lens holder illustrating the circumstance occurring just after inadvertent movement of the head and eye of the patient has occurred—therefore showing a displacement between the patient's pupil and the center of the trial lens.

Referring to FIG. 5A, a schematic of eye E undergoing movement with respect to the trial lens holder 40 is illustrated. This schematic shows the video camera's V view of the eye E as seen through the trial lens holder 40 and the position of trial lens marker LED 58, shown pointing at the video camera V.

Eye E is shown gazing directly at the center of hemispherical projection screen S, but is shown in a state where involuntary motion of the head of patient P has occurred causing motion of the eye E. Thus in FIG. 5A, the eye E is shown deliberately off center in both the horizontal and vertical directions. This indicates that the patient's head moved from a previously centered position and patient P stands the risk of having the trial lens frame obscure a point about to be presented by the field tester.

If eye E moves from the central position, the reflections on the cornea C move also. This causes the reflections 64-67 (bright dots in the video image) to move off center also. The computer must disregard these reflections and find the dark pupil area 60 in the video data in order to find the diameter and the center of the pupil. Thus the four LED illumination sources 54-57 (See FIG. 3B) are placed such that their reflections are least likely to interfere with the major diameter of the pupil and appear overlying the iris 62 of eye E.

Figure 5B:
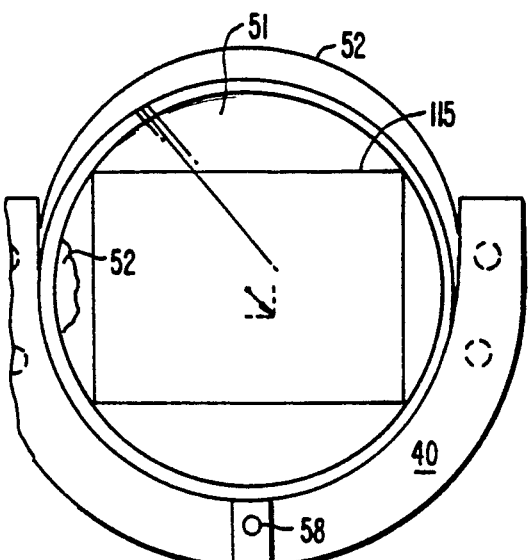
FIG. 5B is a vector plot of the correction required for the centering of the trial lens with respect to the moved patient's eye.
Figure 5C:
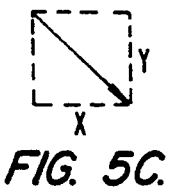
FIG. 5C is an enlarged vector plot illustrating in the form of vectors the stepper motor displacements required.

Referring to FIG. 5B, it is seen the video data is restricted by a window 115 inside the trial lenses 51, 52 to prevent the dark data created by the lens holder 40 from being included in the video data and being mistaken for the pupil 60. Pupil 60 is the only major dark part of the image. When this area is found in the video data, the video line containing the longest dark area is found, the length of the dark area bisected, and the diameter and center of the pupil are calculated.

Given the location of the pupil 60 center and the location of the trial lens holder marker LED 58, the computer can instruct the motor controlling portion of the hardware and software to move the lens to center on the pupil. The offset from the trial lens marker to the center of the lens is a calibrated value for a specific field tester.

Gaze Direction Determination

Referring to FIG. 7A, an additional object of this invention is to determine the actual gaze direction of the eye under field test. This direction is best measured by using the relative position of the pupillary opening 60 and a corneal reflection 140 produced by an infrared source 130 (or 130'; see 1A) on the surface of the hemispherical projection screen S, near the center. For example, if the eye E changes gaze direction slightly, the corneal reflection 140 of source 130 will move at a different rate than the pupil 60. This is due to the fact that the cornea is a portion of a sphere, smaller in diameter than the eye, mounted on the eye. The eye rotates about its center when the gaze is altered which is not the center of the spherical cornea. Hence, by determining the difference between the position of the corneal reflection 140 and the center of the pupil 60, gaze direction can be readily derived.

It will be realized, however, that all corneas are not absolutely spherical. Consequently, it is required at the beginning of the field test that an initial reading be taken and used during the test as a reference. Under controlled circumstances where it is known that the patient is properly fixated, the relationship between the center of the pupil and the corneal reflection 140 is stored as a reference. This relationship can be used during the test to determine the actual real time gaze direction. It will be understood that if the eye moves, because the patient's head moves from the center of the bowl, and the patient is still properly fixated, the measured fixation may change.

An advantage of the disclosed method for determination of the fixation of the eye is that since the absolute eye position with respect to the bowl is known by the lens positioning protocol, that part of the measured fixation change due solely to eye change in position may be calculated and subtracted from the measurement. This independence allows the eye to be moved away from the center of the spherical projection screen S, since the lens will track to center on the pupil.

An additional object of this invention is to allow gaze measurement to be independent of the distance from the eye to the trial lens holder. A central reflection, known as the gaze reflection, is generated by an LED 130 placed on the surface of the screen S, near the center, pointing toward the patient P. This LED source 130 produces a corneal reflection near the center of the pupillary opening, when the patient is fixated at the center of the screen S. The gaze reflection 140 position is independent of the closeness of the eye to the trial lens, since the source is relatively distant from the eye.

An additional object of this invention is to disclose alternate protocols for the placement of the light source for determining gaze direction. It should be noted that the reflection from the cornea is very efficient. Referring briefly to FIG. 1A, turning ON the gaze direction source 130 or 130', 30 cm from the eye, contributes very little to the illumination of the iris compared to the four illumination LEDs in the lens holder, while generating a bright dot of light on the cornea. This allows the video data with source 130 or 130' ON to be subtracted from the data with the source OFF. The resulting data will be the only major change, the corneal reflection. The position control computer can adjust the brightness of source 130 or 130' to make the corneal reflection at maximum brightness without interacting with the brightness of the image.

According to a first embodiment, the LED placed on the projection screen surface is used to create the central corneal reflection. In this embodiment, light source 130' for the reflection is placed near the exact center of the screen, on line with the camera's optical center. This illuminates the pupil with light reflected from the retina.

According to a second and preferred embodiment, the LED placed on the screen surface is offset as at position 130 so as not to create a retinal reflection. The offset is sufficient to maintain a dark pupil by returning the light reflected by the retina to the source, rather than the camera.

An advantage of both protocols is that they generate a central corneal reflection, one with a light background and one with a dark background.

A disadvantage of the central corneal reflection from central light source 130' is that the brightness of the retina is a function of the square of the pupil diameter, since the iris acts as a restriction to the light entering the eye. Another disadvantage is that the source 130' blocks some of the light returning to the video camera and the reflection of the source has less contrast on the lighted pupil. Also the subtraction of the data with source 130' ON from the data with 130' OFF will detect two changes, the lighted pupil and the added central corneal reflection.

Because light source 130 is offset with respect to the optical axis of the video camera V, the pupil appears dark. This dark pupil illumination of light source 130 has the advantage that the resultant dark pupil remains equally as dark, independent of pupil diameter. This method of utilizing a dark pupil yields a high contrast between the pupil and the corneal reflection. As a consequence, the corneal reflection in the pupil is easier to locate.

It will be understood that the dark pupil illumination of light source 130 is preferred if the center of the pupil is determined with the gaze direction determination reflection LED source ON, as the method maintains a dark pupil video image. However, if the pupil center is determined during the lens centering schedule, when the LED is off, either type of illumination can be used, since both methods make a central corneal reflection needed for gaze direction determination.

It will be understood by reference to the protocol for the interrelation of lens centering and gaze determination, that an alternating protocol is preferred. Specifically, during lens centering the light source 130 or 130' is extinguished. During gaze tracking, light source 130 or 130' is illuminated. This method of illumination is termed the "alternating illumination protocol."

An advantage of the alternating illumination protocol for separating trial lens centering from gaze direction determination is that it eliminates the interaction between the gaze direction central reflection and the determination of the pupil center. It will be understood that randomly selected corneas are not perfectly spherical. Certain patients have cornea shapes which place the gaze direction central reflection at the edge of the pupil. This is also true when the patient is poorly fixated. The bright gaze direction determination corneal reflection in the video data can interfere with the determination of the left or right pupil edge if the alternating illumination protocol were not used.

A disadvantage of the alternating illumination protocol is that it does cause the accumulation of data for the determination of the center of the pupil to be delayed by one frame (0.03 seconds) from the accumulation of data for the central reflection position. This delay makes a gaze direction determination error possible if the patient moves abruptly.

Figure 6:
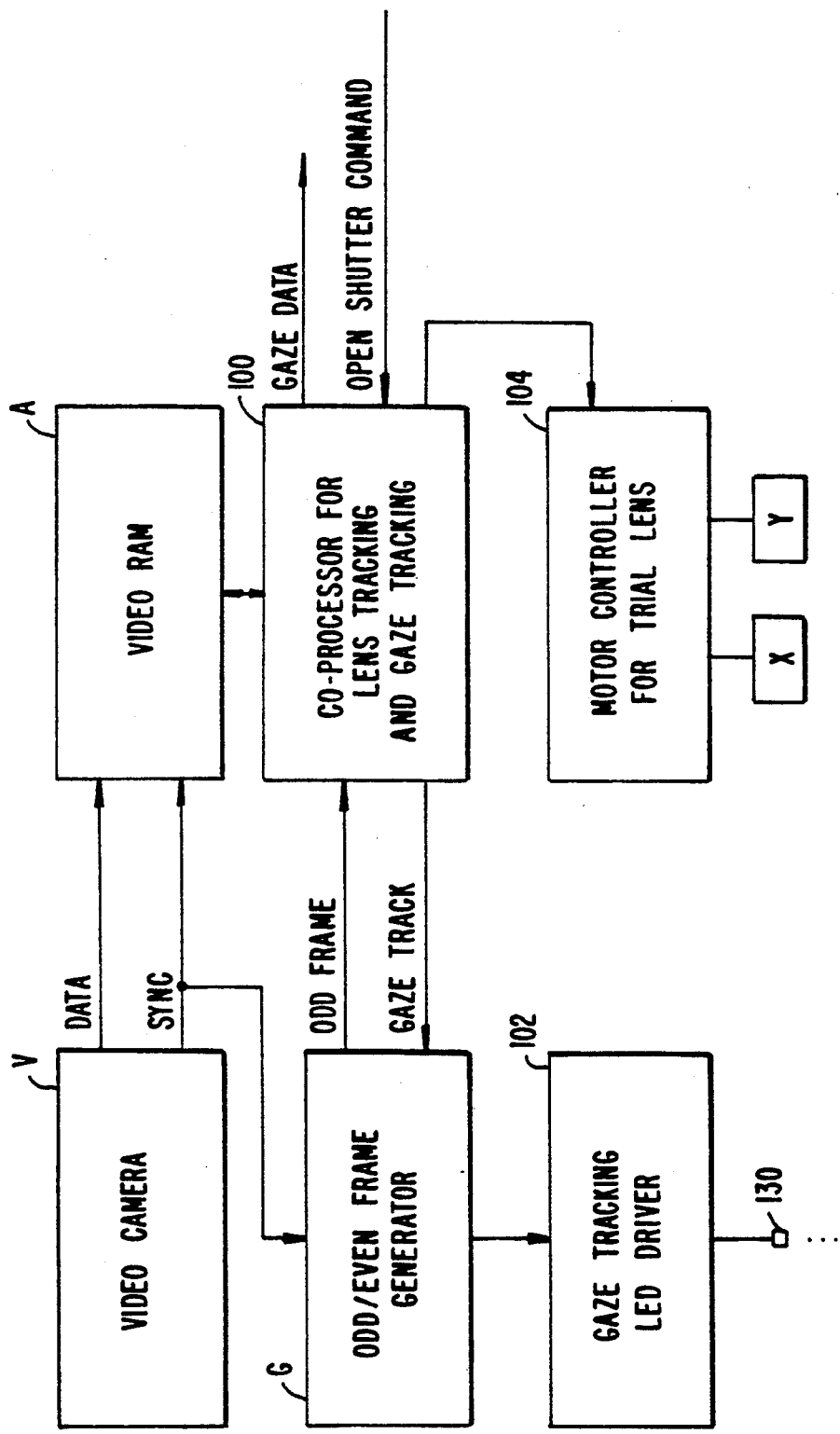
FIG. 6 is a block diagram illustrating the software logic required for centering the moveable trial lens relative to the video view of the eye of said patient.

Referring to FIG. 6, a schematic of computer system and gaze illumination control is set forth. It will be understood that the schematic here illustrated is implemented in software. Accordingly, there is attached hereto a microfiche appendix containing an applicable listing that is suitable for the implementation of this invention.

The computer system consists of six major components:

1. Video Camera V is a conventional image conversion device capable of changing an infrared illuminated scene into a serial stream of analog data. The scene is scanned from top to bottom into the conventional set of horizontal lines, termed a scan or field. The camera may be of the interlace type, producing two scans, each offset by half a vertical line spacing to form a complete image comprised of two sequential scans. This is termed a frame.

2. Video RAM A is a block of electronic memory which contains electronic processors for changing the analog video data from the video camera into a digital form and storing digital data under the control of the position control computer in an electronic memory or RAM (random access memory). The data from the video camera is synchronized into lines, scans, and frames by the conventional synchronization apparatus. This is a standard item of manufacture sold under the mark Matrox by the Matrox Company of Dorval, Quebec, Canada. The model used was model MIP-512.

3. Odd/Even Frame Generator G is a hardware block that determines the completion of a video frame from the video camera synchronization. This could cause the gaze direction determination reflection generator (LED) to be illuminated on alternate frames of the video data if the gaze direction determination mode is selected by the position control computer. This hardware element is a simple binary element, dividing the frame clock by two to schedule the gaze tracking illumination on alternate frames.

4. The position control computer 100 controls lens centering and makes gaze direction determination. The position control computer responds to commands from another computer for the operation of the field tester proper, termed the main computer. The main computer sends commands to open the shutter, thereby presenting the point. This is the signal to determine gaze direction, since the point is about to be presented. The position control computer returns the gaze direction data to the main computer for analysis. Position control computer 100 is sold under the mark SBE by SBE, Incorporated, of Concord, Calif.

5. Gaze direction determination LED driver 102 contains an LED driver for the gaze direction determination source. This constitutes a simple transistor switch for turning on and off light source 130 or 130'.

6. Motor controller 104 contains the hardware necessary to operate the motors which move the lens. These constitute conventional stepper motor controllers. The position control computer schedules a move if it determines that the trial lens is not properly centered on the pupil and transmits the motion required to re-center the lens to the controllers for execution.

The video camera V is of the conventional scan type, changing the image of the eye E into a sequence of data scanned horizontally into lines, scanning from top to bottom. This scan data is converted to a digital form and stored in an electronic memory in video RAM A. The video data contains an image of the eye and the trial lens holder. There should be a dark pupil image and a bright dot of light generated on the trial lens holder to locate the trial lens holder and position the video window which restricts the video data to the area circumscribed by the trial lens frame. If the dark pupil image does not occur, it is assumed that the eyelid is closed and no trial lens movements should be made. If the video window is dark, it is assumed that a patient is not present and no trial lens movements should be made.

The coordinates of image features, such as trial lens holder marker and the pupil/iris boundaries, are conventionally determined by the software system based upon their line and dot addresses.

Referring to FIG. 7A, a schematic of eye E with varied gaze direction with pupil 60 centered in trial lens frame 40 is illustrated. This schematic shows the video camera's V view of eye E as seen through the trial lens 40 and the position of trial lens marker LED 58, shown pointing at the video camera V. Eye E is shown not gazing at the center of the hemispherical projection screen S but with the pupil 60 in the center of the lenses 51, 52. This is the assumed position of the pupil 60 since the trial lens centering activity has occurred prior to the start of the gaze tracking activity.

The reflections of the illumination sources 64-67 are not central to the lens or the pupil since eye E is not centered in the lens. Only the pupil 60 is centered in lenses 51, 52.

The video window 125 used for gaze direction determination is much smaller, about one sixteenth of the area of the window 115 for lens centering (compare FIG. 5B). This restricts the area of interest sufficiently to exclude the possible reflections from the trial lens surfaces 141 and 142. These unwanted reflections are generated mainly by high power trial lenses where the tipping of the lenses is not totally effective. Tipping however does cause the reflections to be non-central, which would otherwise confuse the location of the central reflection. The trial lenses are tipped with respect to the axis of the camera, preferably downward, to place the reflections of the gaze direction determination source 130 or 130' at the top and bottom of the lens, away from the central window. (See reflexes 141, 142 as exemplary reflections.)

It will be understood that gaze direction determination must be done with more precision than the trial lens holder 40 positioning. Gaze direction determination must detect changes of video data which challenge the resolution of the video camera V. This is necessary to determine small changes in gaze direction. Trial lens positioning has a lower resolution function of positioning the lens to the approximate center of the patient's pupil; therefore, great precision is not required.

The gaze direction determination reflection source 130 or 130' is turned on and the video data is stored in a portion of the RAM which allows the central data from the previous frame to be maintained. This allows the lens centering data to be preserved such that a more accurate determination of the pupil center can be made if a crude determination was made during lens tracking.

The gaze direction can be calculated from the pupil center and the gaze tracking reflection location. In practice an initial calibration of the location of these points is made when the patient is properly fixated at the start of the field test. This calibration value is used subsequently as a reference for gaze direction determination.

Figure 8:
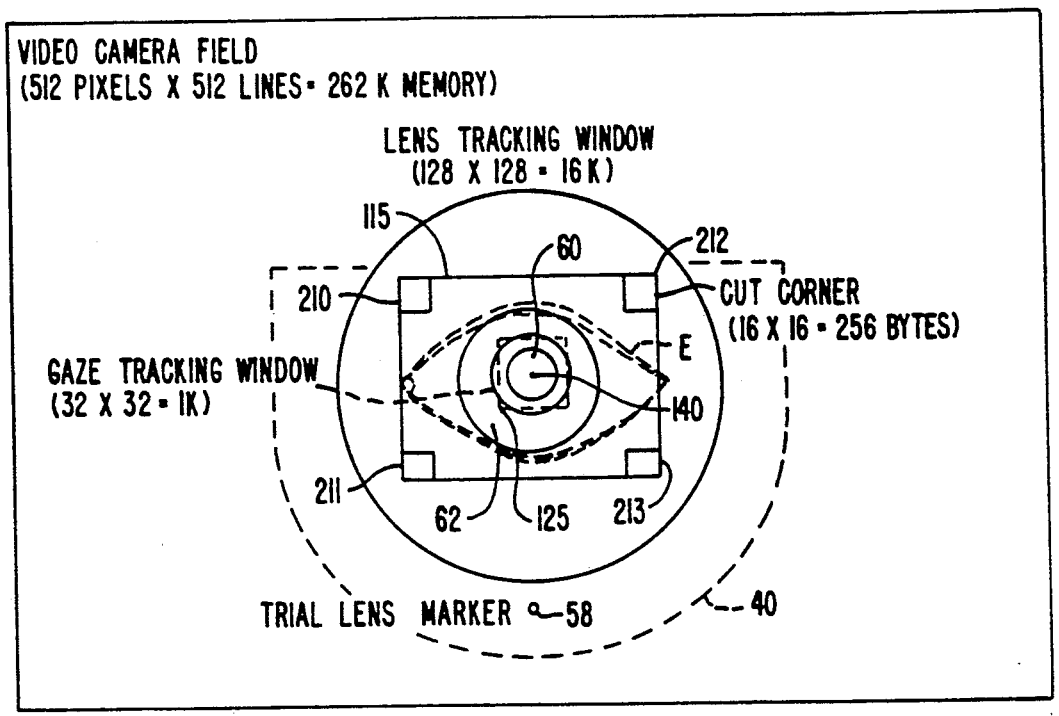
FIG. 8 is an illustration of the video camera field with two sizes of video window overlaid on the field, a first portion of the video field overlays the current position of the trial lens and another smaller central portion is used for measuring gaze direction of the patient during test.
Figure 10A:
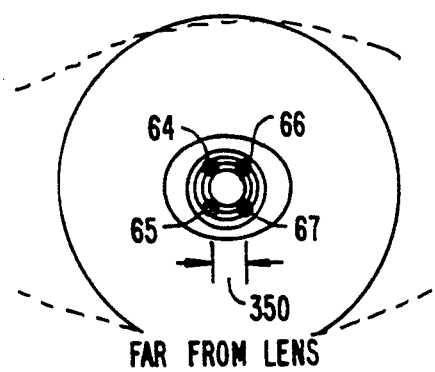
Figure 10B:
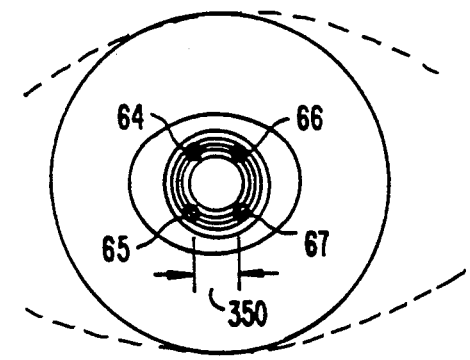
Figure 10C:
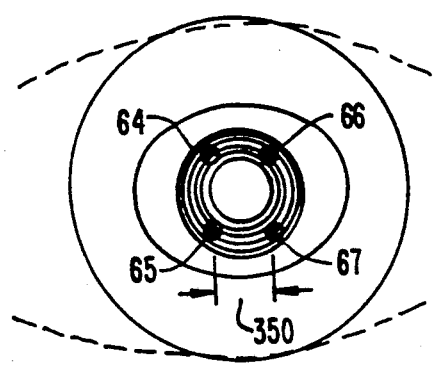
Figure 10D:
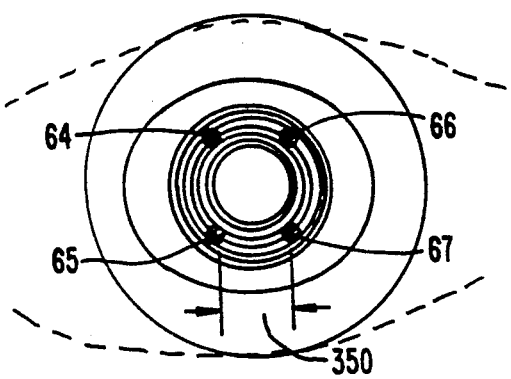

Referring to FIG. 8, a diagram of the RAM address map for lens tracking and gaze tracking are illustrated overlying one another. The larger lens tracking video picture is illustrated at 115. The smaller gaze tracking video picture is illustrated at 125.

The RAM (random access memory) contains sufficient memory to store one sixteenth of the video data output by the video camera V. Since the field of view of the camera must cover a large area to allow the eye to be located non-centrally in the trial lens, the total video field of view of the camera exceeds by many times the field needed for lens positioning. The size of the eye image on the video camera field is a trade-off between field of view and resolution. The lens tracking window 115 is shown in the center of the camera's field of view, but will move to other positions based upon the location of the trial lens holder marker. It will always be centered in the lens.

This window 115 is moved by the position control computer to fit inside the trial lens area based upon the location of the last bright video artifact, the marker 58 of the trial lens holder 40. The size and centering of the window is important, as this is the method for excluding the dark area caused by the trial lens holder 40, which otherwise might be confused for the pupil, and the reflections from the trial lens frame which could be confused as central corneal reflections.

The gaze direction determination window 125 comprises only a small portion of the larger lens centering window 115. Specifically, this gaze direction determination window is created by mapping out corners 210-213 from the corners of the lens centering window 115. This mapping at the corners does not significantly interfere with the lens centering function and enables the corners to be beneficially utilized to store the small central window. The video data stored in the four corners are combined automatically by hardware to form a data area in the small central window. This small window is large enough to store the image of the pupil with the corneal reflex 140 since the pupil has been centered by the lens centering system prior to gaze direction determination.

Having set forth the disclosed video maps it will be understood that lens centering and gaze direction determination includes five closely interrelated functions. These functions are:

1. To move (track) the trial lens to center same on the patient's pupil;

2. To determine if the patient's eyelid is closed (no dark area in lens centering window), or if no patient is present (no light area in the lens centering window);

3. To measure the patient's real time gaze direction;

4. To measure the real time pupil diameter; and

5. To (optionally) check the closeness of the eye to the trial lens.

Figure 9:
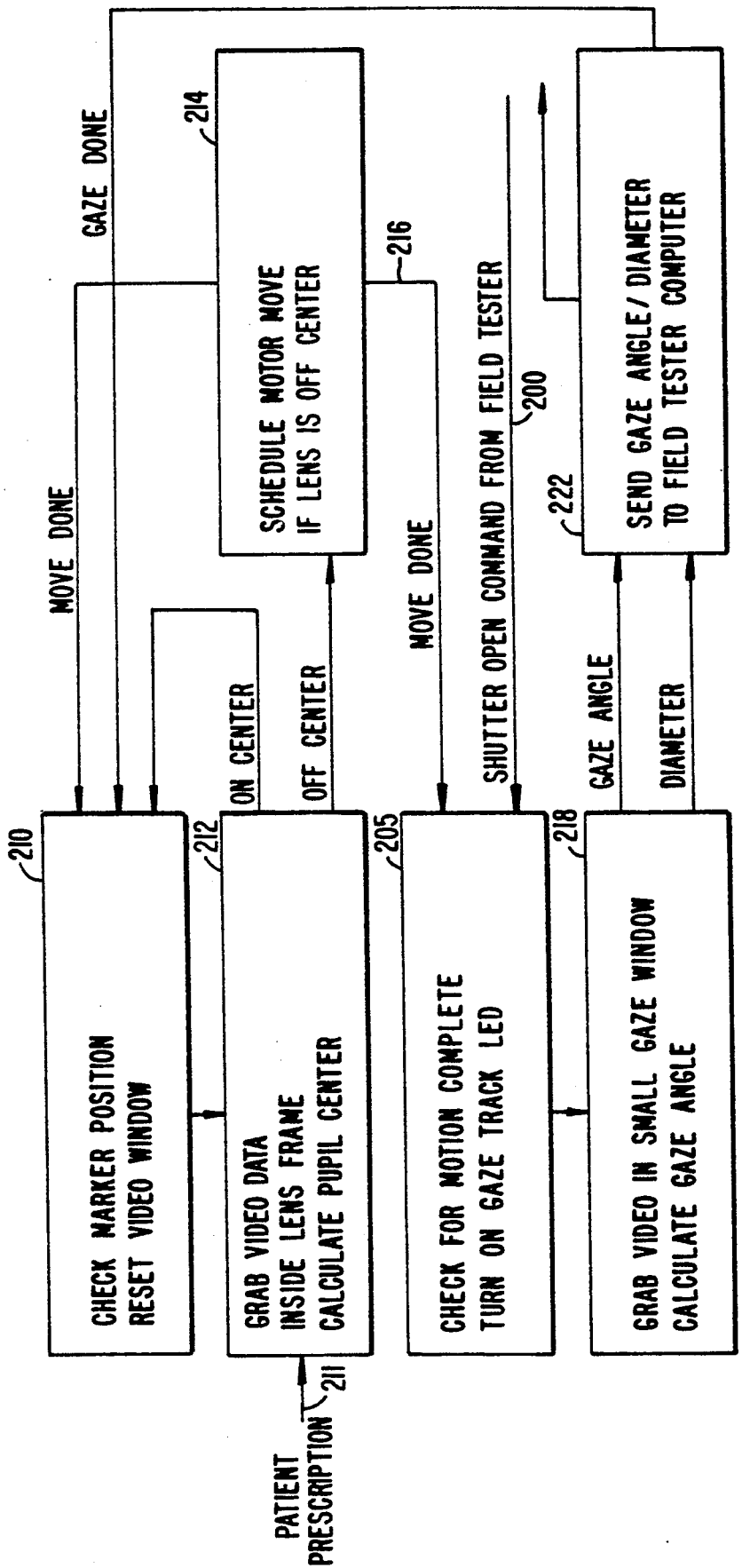
FIG. 9 is a software logic schematic of program logic required for the detection of the fixation or gaze direction of the patient, and, FIGS. 10A–10D are schematic representations for the recognition of the distance of the eye relative to the trial lens for maintaining the patient at the correct distance with respect to the trial lens.

Referring simultaneously to FIGS. 8 and 9, the logic utilized in both lens centering and gaze direction determination can be understood. Explanation will first be offered emphasizing the small central memory window 125 used to determine gaze direction. Thereafter, reference will be made to the schematic of FIG. 9 for setting forth the overall coordination of the disclosed software.

It should be understood that it is necessary to interrelate the protocols of the instrument so that the various tracking functions can occur without interference with respect to one another. Accordingly, the pupil center and diameter are determined during lens centering activity or during gaze tracking, before the gaze tracking source 130 or 130' is turned on. The central corneal reflection is generated during the gaze direction determination activity, occurring briefly before and during the point presentation. This separation of activity keeps reflections from the surface of the trial lens caused by the gaze tracking source 130 or 130' from interfering with dark pupil position determination.

An advantage of the gaze direction determination protocol is that the system has a secondary output of the real time pupil diameter. This can be used as a replacement for the patient response push button since a small change in pupil diameter occurs when a point is presented and recognized. While this expedient has liberally been suggested elsewhere, it is a useful result of this disclosure that change of pupil diameter 60 can be measured.

An additional advantage of the lens centering and gaze direction protocols is that the system also generates data concerning the stability of the patient's head position and gaze direction as a function of time. This can be used as an indicator of test validity, since the lens should require little adjustment if the patient is comfortable and there should be little change in gaze direction if the patient is alert.

Gaze direction determination can be simply summarized. Referring to FIG. 9, when the shutter is commanded open at 200, the field tester begins the preparation for placement of a point 16 on the surface of screen S. The position control computer delays the opening of the shutter and schedules gaze direction determination.

Prior to starting gaze direction determination, a check is made to see that the lens is not moving and that there is a complete frame collected after the motion last stopped. If this is not the case, the gaze direction determination waits for these conditions of the lens not moving and collection of a complete frame to occur.

The gaze direction determination reflection source 130 or 130' is turned on and the addressing of the RAM is changed in hardware to the map set forth at 125 in FIG. 8. The purpose of this map change is to save the last frame used by the lens centering procedure (a dark pupil with no central corneal reflex) and to write over the data in the corners 210-213 to store the central gaze tracking video window 125 (dark pupil with a central corneal reflex).

The corners 210-213 are used since the pupil is centered when the gaze direction determination procedure is called. The hardware makes the corners of the RAM appear to be contiguous and in the center of the lens.

The corneal reflection 140 can be found by the software subtraction of the data in the center of the larger lens centering window from the data in the smaller gaze direction determination window. The major difference between these two images is the addition of the central corneal reflection 140. Subtracting allows the gaze direction determination reflection 140 to appear in the pupil area 60 or the iris area 62 without confusion. This occurs in a patient with a small pupil, non-spherical cornea, and/or severe gaze angle error.

An additional object of this invention is to disclose a sequential method of determining the trial lens centering position and gaze direction determination. The field analyzer test here improved consists of the sequential presentation of points on the screen. These points are presented about once per second for about a duration of 0.2 seconds. The gaze direction is of interest directly before presenting the point and during the presentation of the point. At other times the gaze direction is of little interest, as a point is not being presented.

Since the lens holder 40 is moved slowly, so as not to distract the patient P, lens centering is scheduled for the time required to position the projector 14 to the next light point 16. Gaze direction determination is scheduled for the time before and during the light point presentation. This allows the infrared source on the projection screen, used to generate the central reflection 140, to be turned off during the lens tracking activity and on during the gaze angle determination activity.

An advantage of extinguishing the gaze direction determination source 130 or 130' utilized for gaze direction determination during lens centering is present. This extinguishment of the source 130 or 130' has the effect of eliminating the generation of infrared reflections from the trial lenses 51, and 52. These infrared reflections from the trial lenses 51 and 52 might otherwise form bright areas in the image which can interfere with the determination of pupil 60 location.

Referring to FIG. 7B, it is a further object of this invention to prevent the interference of other reflections generated by the gaze direction determination source 130 or 130'. As noted above, the gaze direction determination LED source 130 on the screen S may cause other reflection data to occur in the field of view of the camera from the surfaces of the trial lenses 51 and 52. To avoid these unwanted reflections, the assumption is made that the trial lens is properly centered and that the small video window will exclude said unwanted reflections. Further, the trial lenses 51, 52 are tipped by an angle $\alpha$ (See FIG. 1A), an amount to assure that trial lens reflections from the gaze direction determination source 130 or 130' are directed away from the camera for low power lenses and are centrally displaced for relatively strong lenses.

Referring specifically to FIG. 7A and assuming this position of reflection displacement in the trial lenses, a central video window 125 is generated with respect to the center of the trial lenses 51 and 52. Data outside the window is not considered. The window 125 is centered on the center of the lens, a position determined by a fixed offset from the marker on the trial lens holder, or determined by the absolute position of the trial lens holder if the lens holder marker is not used. The window discards the reflections from the trial lens holder and trial lens surfaces from consideration.

Referring to FIG. 9, it will be remembered that there are two principal activities carried out by the software. One activity is the motion of the motors X and Y to center the lens holder 40 with respect to the image of the pupil 60. The other activity is the calculation of gaze direction of the eye and the diameter of the pupil.

At the end of each frame of video, the hardware is checked to see if the trial lens holder marker has moved significantly. This check occurs at logic 210. If such significant movement has occurred, the video window is re-aligned to fit inside the lens (see FIG. 5B). This realignment should only happen after the motors have moved the lens, but may occur through interaction with the patient moving the lens.

The amount of motor movement which should re-center the lens is calculated (see 212) and the amount the motors must move is scheduled (see 214). The patient's prescription (see 211) is a necessary parameter for this calculation and is input at the beginning of the field test, as the power of the lens changes the apparent size of the eye and changes the apparent distance to re-center same. Motor activity terminates the lens centering and gaze direction determination activity until the move is complete to reduce servo hunting (see lead 216 disabling gaze tracking activity).

When the shutter is scheduled to be opened as signaled at input 200 from the prior art field tester, the video system waits for the motor motion to complete and requires at least one complete frame of video data before proceeding. It then turns on the gaze direction determination generator and stores the data in RAM (see 218). The gaze angle and pupil diameter are reported to the main computer for review. See line 222. If within limits, the shutter is opened and the point is presented.

The gaze tracker may be asked to review the gaze during the point presentation. This requires an alternation between lens and gaze tracking to obtain the two camera fields necessary to measure gaze.

A further object of this invention is to enable the field test video protocol to monitor the closeness of the patient with respect to the trial lens holder. It will be realized that as the eye E moves away from the trial lens holder, the field of view through the trial lens holder 40 will be reduced. It will be appreciated that as the eye moves back from the lens, the reflections generated by the lens holder sources will move toward the center of the eye and therefore become closer together. This is due to the angle of the four illumination sources to the eye. The position control computer locates the two lower reflections 65 and 66 in FIG. 7A of the illumination sources 55 and 57 in FIG. 3B and generates a closeness error if the reflections move in proximity close together inside of a predetermined limit. A simpler functional method, not quite as effective, is to measure the change in position of reflection 65 as compared to the marker 58. If the pupil is centered and the gaze is within the limits, the said comparison is a fair indication of closeness.

An advantage of both the lens centering and closeness detection protocols is that these protocols reduce test errors caused by obscuring the patient's field of view. Lens centering eliminates the fixed alignment requirement of the patient to the instrument. Closeness testing prevents the patient's viewing angle through the trial lens holder from being reduced to the point where an artificial scotoma is generated by the opaque trial lens holder.

Referring to FIGS. 10A-10D, a schematic of the eye at various distances to the trial lens is illustrated. FIG. 10A-10D shows four exaggerated views of the eye with various closeness to the trial lens. It shows a significant change in the spacing 350 between the reflections of the illumination sources.

This change in spacing could be used to detect the patient's retraction from the lens, a condition just as serious as being off center in the lens. Obviously as the patient retracts from the lens the frame has the possibility of obscuring the view of specific points presented on the hemispherical projection screen due to the decreasing viewing angle through the lenses caused by the patient's retraction from the trial lens holder 40.

The lower two reflections 65, 67 are preferred since the eyelid may obscure the upper two reflections when partially closed. The differences in the spacing caused by trial lens magnification can be eliminated by calibrating a specific patient at the start of the test when the nearness to the lens is known and the lens is in place. To avoid confusion with other reflections which may be present the two bottom reflections 65, 67 can be found by starting at the lower pupil/iris boundary and working out in both directions. The nearness detection procedure may be done on an infrequent basis or added as part of the lens centering or gaze direction determination activity. The closeness of the eye to the trial lens alters the magnification of the eye as seen by the camera and thereby effects the accuracy of gaze direction determination. The closeness data can be used as a correction factor.

What is claimed is:

1. In a field test apparatus for monitoring the field of retinal vision of an eye of a patient by projecting light images of variable intensity peripherally to a line of sight along which patient fixation of said eye occurs, said field test apparatus comprising:

a fixation source for view by said eye of said patient along said line of sight;

a screen mounted about said fixation source for receiving the projection of light forming said images, said screen centered about said line of sight to enable said eye of said patient fixating along said line of sight at said fixation source to peripherally view images of varying intensity projected to said screen for mapping of the optical sensitivity of a retina of said eye;

means for recording patient indication of said view of said images of said point of light responsive to input from said patient;

means for projecting said images of varying intensity at known different variable placements to said screen relative to said line of sight for measurement of the retinal field of view of said eye of said patient;

means for holding at least one trial lens in front of said patient at the eye of said patient undergoing test;

means for resting a portion of a head of said patient with the eye of said patient proximate to an intersection with said line of sight and said means for holding at least one trial lens;

means for video monitoring of said patient mounted to said screen for providing a video view of the eye of said patient along an axis;

means for dark eye illumination of said eye of said patient including a light source illuminating said eye from a position off center with respect to said axis of said means for video monitoring of said eye;

a gaze direction determination source mounted to said screen for producing on said cornea of said eye a reflection which is a function of the position of said cornea of said eye relative to said line of sight;

means for processing of said video image at a pupil of eye for locating the center of the pupil of said eye and outputting a first signal and outputting a second signal relating to the position of said reflection of said gaze direction determination source in said eye wherein said means for processing said video image includes;

means for measuring a horizontal chord across the pupil of said eye;

means for measuring the vertical distance between a center point on said horizontal chord and the bottom of said pupil of said eye; and, means for determining the center of the pupil of said eye relative to said measured chord and said vertical distance between the center of said chord and said bottom of said pupil of said eye; and, means for comparing said first and second signals and outputting a composite signal related to the direction of gaze of said eye whereby said output changes are a function of eye fixation.

2. The invention of claim 1 and wherein said gaze direction determination light source is on the same optical axis as the video monitoring means.

3. The invention of claim 1 and wherein said gaze tracking light source is offset with respect to the optical axis of the video monitoring means.

4. The invention of claim 1 and wherein said gaze direction determination source includes a light source in a near visible infrared spectrum.

5. The invention of claim 1 and wherein:
said means for holding at least one trial lens includes:
means for tipping said at least one trial lens at an angle with respect to a plane normal to a linear axis intersecting said eye of said patient and said fixation source for displacing the reflection on said trial lens relative to the center of said trial lens.

6. The invention of claim 1 and further including:
means for comparing the position of the pupil in said video view of said eye of said patient to the position of said trial lens to output a signal proportional to the relative displacement of the pupil of said patient and said means for holding at least one trial lens to output a third signal relating to changes in the position of said pupil of said patient relative to said means for holding at least one trial lens;
means for moving said means for holding at least one trial lens responsive to said third signal to maintain a constant relative displacement between said eye of said patient and means for holding at least one trial lens.

7. The invention of claim 6 and including means for switching said gaze direction determination source off during generation of said third signal.

8. The invention of claim 6 and wherein:
means for recording the response of said patient to said peripherally viewed images of varying intensity projected to said screen for mapping the optical sensitivity of the eye's retina;
means for recording the movement of said trial lens and the fixation of said patient with respect to said responses of said patient to said peripherally viewed images of varying intensity whereby said recorded movement and responses can be compared to head movement and fixation change of said patient.

9. The invention of claim 6 and wherein:
said means for holding at least one trial lens includes multiple light sources for illuminating said eye.

10. The invention of claim 6 and wherein:
said means for holding at least one trial lens includes a light source for projection to said means for video monitoring.

11. In a field test apparatus for monitoring the field of retinal vision of an eye of a patient by projecting light images of points of light of variable intensity peripherally to a line of sight along which patient fixation of said eye occurs, said field test apparatus including:

a fixation light source emitting light in a visible spectrum for view by said eye of said patient along said line of sight;

a screen mounted about said fixation source for receiving the projection of light forming said images of points of light, said screen centered about said line of sight to enable said patient at said eye fixating along said line of sight at said fixation source to peripherally view images of said points of light of varying intensity projected to said screen for mapping of the optical sensitivity of an eye's retina;

means for recording said patient's indication of said view of said images of said points of light responsive to input from said patient;

means for projecting said images of points of light of varying intensity at controlled variable placements to said screen relative to said line of sight for measurement of the retinal field of view of said eye of said patient;

means for holding at least one trial lens in front of said patient at the eye of said patient;

means for resting a portion of a head of said patient with the eye of said patient proximate to an intersection with said line of sight and said means for holding at least one trial lens; and means for video monitoring of said patient mounted to said screen for providing a video view of the eye of said patient;

the improvements to said means for holding and said means for video monitoring comprising:

means for comparing the position of a pupil in said video view of said eye of said patient to the position of said trial lens to output the relative displacement between center of the pupil of said patient and said means for holding at least one trial lens, said means outputting a signal responsive to said relative displacement; and means for moving said means for holding at least one trial lens responsive to said detected relative displacement to maintain a constant relative displacement between the center of said pupil of said patient and said trial lens.

12. The invention of claim 11 and wherein said means for moving said means for holding at least one trial lens includes means for outputting the position of said trial lens to said means for comparing.

13. The invention of claim 11 and wherein said means for holding at least one trial lens includes at least one trial lens held between said patient's eye and said hemispherical projection screen.

14. The invention of claim 11 and wherein said means for video monitoring of said patient's eye is sensitive in an infrared spectrum near the end of the visible spectrum.

15. The invention of claim 11 and including means for illuminating the eye of said patient.

16. The invention of claim 15 and wherein said means for the illumination of the eye of said patient is affixed to said means for holding at least one trial lens and is directed from said means for holding at least one trial lens to the eye of said patient.

17. The invention of claim 15 and wherein said means for illuminating the eye of said patient includes illuminating the eye of said patient in a near visible infrared spectrum only.

18. The invention of claim 15 and wherein said means for illuminating the eye of said patient affixed to said means for holding at least one trial lens includes light sources on said means for holding at least one trial lens at the 2, 4, 8 and 10 o'clock positions.

19. The invention of claim 15 and wherein said means for holding at least one trial lens includes means for illuminating the eye of said patient directed toward the eye of said patient and away from said video monitoring means.

20. The invention of claim 15 and wherein said means for holding at least one trial lens includes at least one light source for illuminating the eye of said patient.

21. The invention of claim 20 and wherein said means for holding at least one trial lens includes multiple light sources for generating multiple reflections from said light sources from the cornea of said eye of said patient proximate said line of sight.

22. The invention of claim 11 and wherein said field test apparatus is provided with a video display for said video image.

23. The invention of claim 11 and wherein said means for resting a portion of said head of said patient includes a chin rest for said patient.

24. The invention of claim 23 and wherein said chin rest includes two chin indentations including a first chin indentation for testing the right eye of said patient and a second chin indentation for testing the left eye of said patient.

25. The invention of claim 23 and including means for vertically adjusting said chin rest.

26. The invention of claim 11 and wherein said means for monitoring said video image of said eye of said patient includes means for monitoring the center of said pupil of said patient.

27. The invention of claim 26 and wherein said means for monitoring the center of said pupil of said patient includes means for locating a horizontal chord across said pupil, means for bisecting said horizontal chord, and means for measuring a vertical dimension with respect to said chord to a boundary of said pupil for determining the center of said pupil.

28. The invention of claim 11 and wherein said means for holding at least one trial lens is adjustable between said means for moving and said eye of said patient at a flexible frictional joint for manually varying the towards and away position of said means for holding at least one trial lens with respect to said eye of said patient.

29. The invention of claim 11 and wherein said screen is a hemispherical projection screen provided with means for providing a uniform illumination to said hemispherical projection screen viewed by said patient.

30. The invention of claim 29 and wherein said means for providing a uniform illumination is in the visible spectrum.

31. The invention of claim 11 and wherein said means for holding at least one trial lens includes a light source for projection to said means for video monitoring to indicate the position of said means for holding at least one trial lens.

32. The invention of claim 11 and wherein said means for moving said means for holding at least one trial lens includes first means for moving said means for holding horizontally and second means for moving said means for holding vertically.

33. The invention of claim 32 and wherein said means for moving said means for holding said at least one trial lens includes stepper motors.

* * * * *